(12) United States Patent
Knopf et al.

(10) Patent No.: US 7,625,867 B2
(45) Date of Patent: Dec. 1, 2009

(54) BMP-3 PROPEPTIDES AND RELATED METHODS

(75) Inventors: John Knopf, Carlisle, MA (US); Jabir Seehra, Lexington, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 156 days.

(21) Appl. No.: 11/092,353

(22) Filed: Mar. 28, 2005

(65) Prior Publication Data

US 2005/0272653 A1    Dec. 8, 2005

Related U.S. Application Data

(60) Provisional application No. 60/557,100, filed on Mar. 26, 2004.

(51) Int. Cl.
| | |
|---|---|
| A61K 38/00 | (2006.01) |
| A61K 38/16 | (2006.01) |
| C07K 14/00 | (2006.01) |
| C12N 15/00 | (2006.01) |

(52) U.S. Cl. ............................. 514/12; 514/2; 530/350; 435/69.1; 435/69.7; 424/198.1

(58) Field of Classification Search ........................ None
See application file for complete search history.

(56) References Cited

U.S. PATENT DOCUMENTS

| | | | |
|---|---|---|---|
| 5,637,480 A | | 6/1997 | Celeste et al. |
| 5,808,007 A | | 9/1998 | Lee et al. |
| 5,834,179 A | * | 11/1998 | Jones et al. .................... 435/4 |
| 6,004,780 A | | 12/1999 | Soppet et al. |
| 6,071,708 A | * | 6/2000 | Jones et al. .................. 435/7.1 |
| 6,656,708 B1 | | 12/2003 | Yu et al. |
| 2003/0082233 A1 | | 5/2003 | Lyons et al. |
| 2003/0144176 A1 | | 7/2003 | Olson et al. |
| 2003/0224501 A1 | | 12/2003 | Young et al. |
| 2005/0244867 A1 | | 11/2005 | Soppet et al. |

FOREIGN PATENT DOCUMENTS

| | | |
|---|---|---|
| WO | WO-94/03600 | 2/1994 |
| WO | WO-94/15965 A1 | 7/1994 |
| WO | WO-94/26893 A1 | 11/1994 |
| WO | WO-95/24474 A1 | 9/1995 |
| WO | WO-96/39431 A1 | 12/1996 |
| WO | WO-99/37320 A1 | 7/1999 |
| WO | WO-00/43781 | 7/2000 |
| WO | WO-2001/922298 | 12/2001 |
| WO | WO 02/43759 | * 6/2002 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Wells. J.A. Addivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Himo et al. Coordination of BMP-3b and cerberus is required for head formation of Xenopus embryos. Developmental Biology, 260, 138-157, available on line Jun. 4, 2003.*
Graddis et al., Designing proteins that work using recombinant technologies, Curr. Pharm, Biotechnol., 3, 285, 2002.*
Caricasole, et al., "Human growth-differentiation factor 3 (hGDF3): developmental regulation in human teratocarcinoma cell lines and expression in primary testicular germ cell tumours," Oncogene, 16:95-103 (1998).
Chen, H., et al., "BMP10 is essential for maintaining cardiac growth during murine cardiogenesis," Development, 131(9):2219-2231 (2004).
Clark, et al., "Human Stellar, NANOG and GDF3 Genes are Expressed in Pluripotent Cells and Map to Chromosome 12p13, a Hotspot for Teratocarcinoma," Stem Cells, 22:169-179 (2004).
McPherron, et al., "GDF-3 and GDF-9: two new members of the transforming growth factor-beta superfamily containing a novel pattern of cysteines," Journal of Biological Chemistry, 268(5): 3444-9 (1993).

(Continued)

*Primary Examiner*—Christine J Saoud
*Assistant Examiner*—Elly-Gerald Stoica
(74) *Attorney, Agent, or Firm*—Ropes & Gray LLP

(57) ABSTRACT

The present invention provides compositions and methods for promoting bone growth. The present invention also provides methods of screening compounds that modulate BMP-3A or BMP-3B activity. The compositions and methods provided herein are useful in modulating bone growth.

14 Claims, 13 Drawing Sheets

OTHER PUBLICATIONS

Neuhaus, H., et al., "Heart specific expression of mouse *BMP-10* a novel member of the TGF-β superfamily," Mechanisms of Development, 80:181-184 (1999).

Pashmforoush, M., et al., "Nkx2-5 Pathways and Congenital Heart Disease: Loss of Ventricular Myocyte Lineage Specification Leads to Progressive Cardiomyopathy and Complete Heart Block," Cell, 117:373-386 (2004).

Jun et al., "Coordination of BMP-3b and cerebus is required for head formation of Xenopus embryos", Developmental Biology, 260(1):138-157(2003).

Constam et al., "Regulation of Bone Morphogenetic Protein Activity by Pro Domains and Proprotein Convertases", The Journal of Cell Biology, 144(1):139-149(1999).

Nagaso et al., "Dual Specificity of Activin Type II Receptor ActRIIb in Dorso-Ventral Patterning During Zebrafish Embryogenesis", Development Growth and Differentiation, 41(2)119-133(1999).

Takao et al., "Identification of Rat Bone Morphogenetic Protein-3b (BMP-3b), a New Member of BMP-3", Biochemical and Biophysical Research Communications, 219(2)656-662(1996).

Daluiski et al., "Bone Morphogenetic Protein-3 is a Negative Regulatory of Bone Density", Nature Genetics, 27(1):84-88(2001).

Hino et al., "Bone Morphogenetic Protein-3B (BMP-3B) Gene Expression is Correlated with Differentiation in Rat Calvarial Osteoblasts", Biochemical and Biophysical Research Communications, 256(2):419-424(1999).

Faucheux et al., "Opposing Actions of BMP3 and TGF beta1 in Human Bone Marrow Stromal Cell Growth and Diffentiation", Biochemical and Biophysical Research Communications, 241(3):787-793(1997).

Hino et al. "Bone Morphogenetic Protein-3 Family Members and Their Biological Functions," Frontiers in Bioscience, 9:1520-1529(2004).

Teichmann, U., and Kessel, M., "Highly restricted BMP10 expression in the trabeculating myocardium of the chick embryo," Dev Genes Evol., 214:96-98 (2004).

Wang, et al., "GDF-3 is an adipogenic cytokien under high fat dietary condition," Biochemical and Biophysical Research Communications, 321:1024-1031(2004).

Witthuhn, et al., "Upregulation of Bone Morphogenetic Protein GDF-3/Vgr-2 Expression in Adipose Tissue of FABP4/aP2 Null Mice," Cytokine, 14:129-135 (2001).

* cited by examiner

Figure 1. BMP-3A propeptide sequence designed as SEQ ID NO: 1 (340 aa).

ERPKPPFPELRKAVPGDRTAGGGPDSELQPQDKVSEHMLRLYDRYSTVQAARTPGSLEG
GSQPWRPRLLREGNTVRSFRAAAAETLERKGLYIFNLTSLTKSENILSATLYFCIGELG
NISLSCPVSGGCSHHAQRKHIQIDLSAWTLKFSRNQSQLLGHLSVDMAKSHRDIMSWLS
KDITQFLRKAKENEEFLIGFNITSKGRQLPKRRLPFPEPYILVYANDAAISEPESVVSS
LQGHRNFPTGTVPKWDSHIRAALSIERRKKRSTGVLLPLQNNELPGAEYQYKKDEVWEE
RKPYKTLQAQAPEKSKNKKKQRKGPHRKSQTLQFDEQTLKKARRK

Figure 2. BMP-3B/GDF-10 propeptide sequence designed as SEQ ID NO: 2 (335 aa).

SHRAPAWSALPAAADGLQGDRDLQRHPGDAAATLGPSAQDMVAVHMHRLYEKYSRQGAR
PGGGNTVRSFRARLEVVDQKAVYFFNLTSMQDSEMILTATFHFYSEPPRWPRALEVLCK
PRAKNASGRPLPLGPPTRQHLLFRSLSQNTATQGLLRGAMALAPPPRGLWQAKDISPIV
KAARRDGELLLSAQLDSEERDPGVPRPSPYAPYILVYANDLAISEPNSVAVTLQRYDPF
PAGDPEPRAAPNNSADPRVRRAAQATGPLQDNELPGLDERPPRAHAQHFHKHQLWPSPF
RALKPRPGRKDRRKKGQEVFMAASQVLDFDEKTMQKARRK

Figure 3. BMP-3A precursor sequence designed as SEQ ID NO: 3 (NP_001192, 472 aa).

MAGASRLLFLWLGCFCVSLAQGERPKPPFPELRKAVPGDRTAGGGPDSELQPQDKVSEH

MLRLYDRYSTVQAARTPGSLEGGSQPWRPRLLREGNTVRSFRAAAAETLERKGLYIFNL

TSLTKSENILSATLYFCIGELGNISLSCPVSGGCSHHAQRKHIQIDLSAWTLKFSRNQS

QLLGHLSVDMAKSHRDIMSWLSKDITQFLRKAKENEEFLIGFNITSKGRQLPKRRLPFP

EPYILVYANDAAISEPESVVSSLQGHRNFPTGTVPKWDSHIRAALSIERRKKRSTGVLL

PLQNNELPGAEYQYKKDEVWEERKPYKTLQAQAPEKSKNKKQRKGPHRKSQTLQFDEQ

TLKKARRKQWIEPRNCARRYLKVDFADIGWSEWIISPKSFDAYYCSGACQFPMPKSLKP

SNHATIQSIVRAVGVVPGIPEPCCVPEKMSSLSILFFDENKNVVLKVYPNMTVESCACR

Figure 4. BMP-3B precursor sequence designed as SEQ ID NO: 4 (NP_004953, 478 aa).

MAHVPARTSPGPGPQLLLLLLLPLFLLLLRDVAGSHRAPAWSALPAAADGLQGDRDLQRH

PGDAAATLGPSAQDMVAVHMHRLYEKYSRQGARPGGGNTVRSFRARLEVVDQKAVYFFN

LTSMQDSEMILTATFHFYSEPPRWPRALEVLCKPRAKNASGRPLPLGPPTRQHLLFRSL

SQNTATQGLLRGAMALAPPPRGLWQAKDISPIVKAARRDGELLLSAQLDSEERDPGVPR

PSPYAPYILVYANDLAISEPNSVAVTLQRYDPFPAGDPEPRAAPNNSADPRVRRAAQAT

GPLQDNELPGLDERPPRAHAQHFHKHQLWPSPFRALKPRPGRKDRRKKGQEVFMAASQV

LDFDEKTMQKARRKQWDEPRVCSRRYLKVDFADIGWNEWIISPKSFDAYYCAGACEFPM

PKIVRPSNHATIQSIVRAVGIIPGIPEPCCVPDKMNSLGVLFLDENRNVVLKVYPNMSV

DTCACR

Figure 5. Nucleic acid sequence encoding a BMP-3A propeptide, designed as SEQ ID NO: 5 (1020 bp).

```
gagagaccgaagccacctttcccggagctccgcaaagctgtgccaggtgaccgcacggcaggtggtggccc
ggactccgagctgcagccgcaagacaaggtctctgaacacatgctgcggctctatgacaggtacagcacgg
tccaggcggcccggacaccgggctccctggagggaggctcgcagccctggcgccctcggctcctgcgcgaa
ggcaacacggttcgcagctttcgggcggcagcagcagaaactcttgaaagaaaaggactgtatatcttcaa
tctgacatcgctaaccaagtctgaaaacattttgtctgccacactgtatttctgtattggagagctaggaa
acatcagcctgagttgtccagtgtctggaggatgctcccatcatgctcagaggaaacacattcagattgat
ctttctgcatggaccctcaaattcagcagaaaccaaagtcaactccttggccatctgtcagtggatatggc
caaatctcatcgagatattatgtcctggctgtctaaagatatcactcaattcttgaggaaggccaaagaaa
atgaagagttcctcataggatttaacattacgtccaagggacgccagctgccaaagaggaggttacctttt
ccagagccttatatcttggtatatgccaatgatgccgccatttctgagccagaaagtgtggtatcaagctt
acagggacaccggaatttttcccactggaactgttcccaaatgggatagccacatcagagctgcccttcca
ttgagcggaggaagaagcgctctactggggtcttgctgcctctgcagaacaacgagcttcctggggcagaa
taccagtataaaaaggatgaggtgtgggaggagagaaagccttacaagacccttcaggctcaggcccctga
aaagagtaagaataaaaagaaacagagaaaggggcctcatcggaagagccagacgctccaatttgatgagc
agaccctgaaaaaggcaaggagaaag
```

Figure 6. Nucleic acid sequence encoding a BMP-3B propeptide, designed as SEQ ID NO: 6 (1005 bp).

```
agccacagggcccccgcctggtccgcactgcccgcggccgccgacggcctgcaggggga cagggatctcca
gcggcaccctggggacgcggccgccacgttgggccccagcgcccaggacatggtcgctg tccacatgcaca
ggctctatgagaagtacagccggcagggcgcgcggccgggaggggg caacacggtccgcagcttcagggcc
aggctggaagtggtcgaccagaaggccgtgtatttcttcaacctgacttccatgcaaga ctcggaaatgat
ccttacggccactttccacttctactcagagccgcctcggtggcctcgagcgctcgagg tgctatgcaagc
cgcgggccaagaacgcttcaggccgcccgctgccctgggccgcccacacgccagcacct gctcttccgc
agcctctcgcagaacacggccacacaggggctactccgcggggccatggccctggcgcc cccaccgcgcgg
cctgtggcaggccaaggacatctcccccatcgtcaaggcggcccgcgggatggcgagct gctcctctccg
cccagctggattctgaggagagggacccgggggtgccccggcccagcccctatgcgccc tacatcctagtc
tatgccaacgatctggccatctcggagcccaacagcgtggcagtgacgctgcagagata cgacccct tccc
tgccggagaccccgagccccgcgcagcccccaacaactcagcggaccccc gcgtgcgccgagccgcgcagg
ccactgggcccctccaggacaacgagctgccggggctggatgagaggccgccgcgcgcc cacgcacagcac
ttccacaagcaccagctgtggcccagcccc ttccgggcgctgaaacccggccagggcgcaaagaccgcag
gaagaagggccaggaggtgttcatggccgcctcgcaggtgctggactttgacgagaaga cgatgcagaaag
cccggaggaag
```

Figure 7. Nucleic acid sequence encoding the BMP-3A precursor protein, designed as SEQ ID NO: 7 (nucleotides 321-1739 of NM_001201, 1419 bp).

```
atggctggggcgagcaggctgctctttctgtggctggctgcttctgcgtgagcctggcgcagggagagag
accgaagccacctttcccggagctccgcaaagctgtgccaggtgaccgcacggcaggtggtggcccggact
ccgagctgcagccgcaagacaaggtctctgaacacatgctgcggctctatgacaggtacagcacggtccag
gcggcccggacaccgggctccctggagggaggctcgcagcctggcgccctcggctcctgcgcgaaggcaa
cacggttcgcagctttcgggcggcagcagcagaaactcttgaaagaaaaggactgtatatcttcaatctga
catcgctaaccaagtctgaaaacattttgtctgccacactgtatttctgtattggagagctaggaaacatc
agcctgagttgtccagtgtctggaggatgctcccatcatgctcagaggaaacacattcagattgatctttc
tgcatggaccctcaaattcagcagaaaccaaagtcaactccttggccatctgtcagtggatatggccaaat
ctcatcgagatattatgtcctggctgtctaaagatatcactcaattcttgaggaaggccaaagaaatgaa
gagttcctcataggatttaacattacgtccaagggacgccagctgccaaagaggaggttaccttttccaga
gccttatatcttggtatatgccaatgatgccgccatttctgagccagaaagtgtggtatcaagcttacagg
gacaccggaatttccactggaactgttcccaaatgggatagccacatcagagctgccctttccattgag
cggaggaagaagcgctctactggggtcttgctgcctctgcagaacaacgagcttcctggggcagaatacca
gtataaaaggatgaggtgtgggaggagagaaagccttacaagacccttcaggctcaggcccctgaaaaga
gtaagaataaaaagaaacagagaaagggcctcatcggaagagccagacgctccaatttgatgagcagacc
ctgaaaaaggcaaggagaaagcagtggattgaacctcggaattgcgccaggagatacctcaaggtagactt
tgcagatattggctggagtgaatggattatctcccccaagtcctttgatgcctattattgctctggagcat
gccagttccccatgccaaagtctttgaagccatcaaatcatgctaccatccagagtatagtgagagctgtg
ggggtcgttcctgggattcctgagccttgctgtgtaccagaaaagatgtcctcactcagtatttattctt
tgatgaaaataagaatgtagtgcttaaagtataccctaacatgacagtagagtcttgcgcttgcagataa
```

Figure 8. Nucleic acid sequence encoding the BMP-3B precursor protein, designed as SEQ ID NO: 8 (nucleotides 457-1893 of NM_004962, 1437 bp).

```
atggctcatgtccccgctcggaccagcccgggacccgggccccagctgctgctgctgctgccgttgtt
tctgctgttgctccgggatgtggccggcagccacagggccccgcctggtccgcactgcccgcggccgccg
acggcctgcaggggggacagggatctccagcggcaccctggggacgcggccgccacgttgggcccagcgcc
caggacatggtcgctgtccacatgcacaggctctatgagaagtacagccggcagggcgcgcggccgggagg
gggcaacacggtccgcagcttcagggccaggctggaagtggtcgaccagaaggccgtgtatttcttcaacc
tgacttccatgcaagactcggaaatgatccttacggccactttccacttctactcagagccgcctcggtgg
cctcgagcgctcgaggtgctatgcaagccgcgggccaagaacgcttcaggccgcccgctgccctgggccc
gcccacacgccagcacctgctcttccgcagcctctcgcagaacacggccacacagggctactccgcgggg
ccatggccctggcgcccccaccgcgcggcctgtggcaggccaaggacatctcccccatcgtcaaggcggcc
cgccgggatggcgagctgctcctctccgcccagctggattctgaggagagggacccgggggtgccccggcc
cagcccctatgcgccctacatcctagtctatgccaacgatctggccatctcggagcccaacagcgtggcag
tgacgctgcagagatacgaccccttccctgccggagacccgagccccgcgcagcccccaacaactcagcg
gacccccgcgtgcgccgagccgcgcaggccactgggcccctccaggacaacgagctgccggggctggatga
gaggccgccgcgcgcccacgcacagcacttccacaagcaccagctgtggcccagcccttccgggcgctga
aaccccggccagggcgcaaagaccgcaggaagaagggccaggaggtgttcatggccgcctcgcaggtgctg
gactttgacgagaagacgatgcagaaagcccggaggaagcagtgggatgagccgagggtgtgctccggag
gtacctgaaggtggacttcgcagacatcggctggaatgaatggataatctcaccgaaatcttttgatgcct
actactgcgcgggagcatgtgagttccccatgcctaagatcgttcgtccatccaaccatgccaccatccag
agcattgtcagggctgtgggcatcatccctggcatcccagagccctgctgtgttcccgataagatgaactc
ccttggggtcctcttcctggatgagaatcggaatgtggttctgaaggtgtaccccaacatgtccgtggaca
cctgtgcctgccggtga
```

Figure 9. Human Fc sequence. Mutations are shown in red.

THTCPPCPAPELLGGPSVFLFPPKPKDTLMISRTPEVTCVVVD(A)VSHEDPEV
KFNWYVDGVEVHNAKTKPREEQYNSTYRVVSVLTVLHQDWLNGKEYKCK(A)VS
NKALPVPIEKTISKAKGQPREPQVYTLPPSREEMTKNQVSLTCLVKGFYPSDIA
VEWESNGQPENNYKTTPPVLDSDGPFFLYSKLTVDKSRWQQGNVFSCSVMHEAL
HN(A)HYTQKSLSLSPGK*

Figure 10. SDS-PAGE analysis of BMP3 pro-MuIgG2a peptide Fc purified using Protein A affinity step.
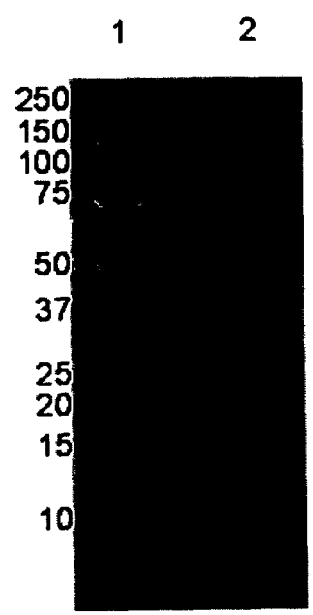

Figure 11. BMP3 pro-MuIgG2a peptide binds mature BMP-3.
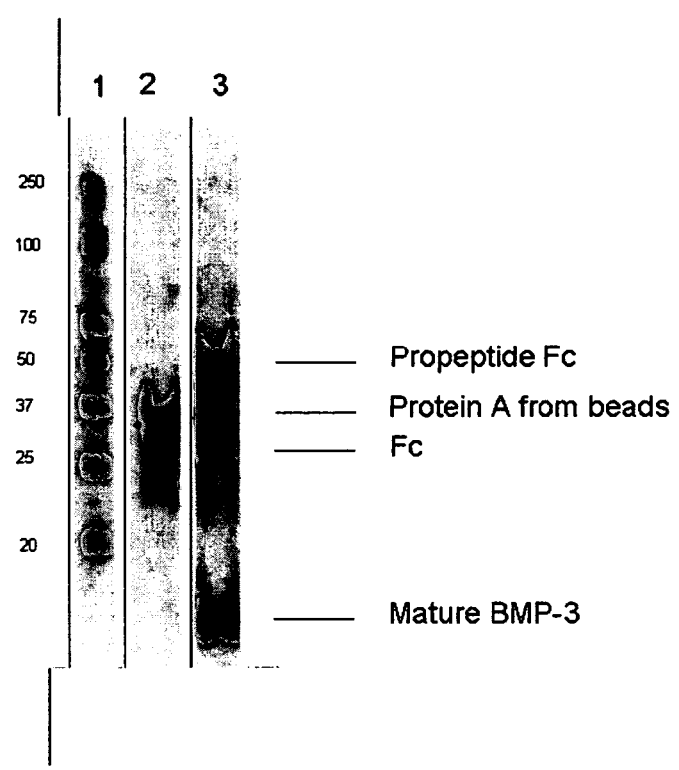

Figure 12. Purified BMP3 pro-MuIgG2a binds to mature BMP-3.
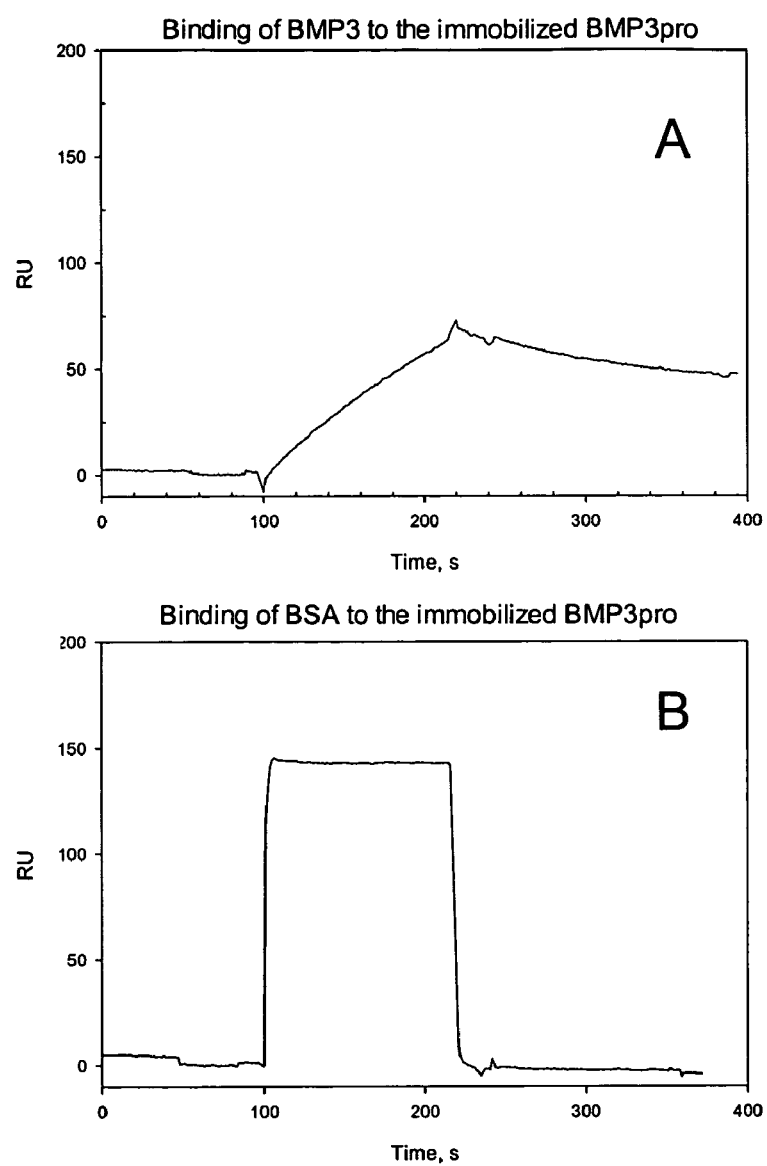

Figure 13. Mature BMP-3 binds to Activin Receptor IIa (ActRIIa) and BMP3 pro-MuIgG2a Fc competes with ActRIIa binding to BMP-3.
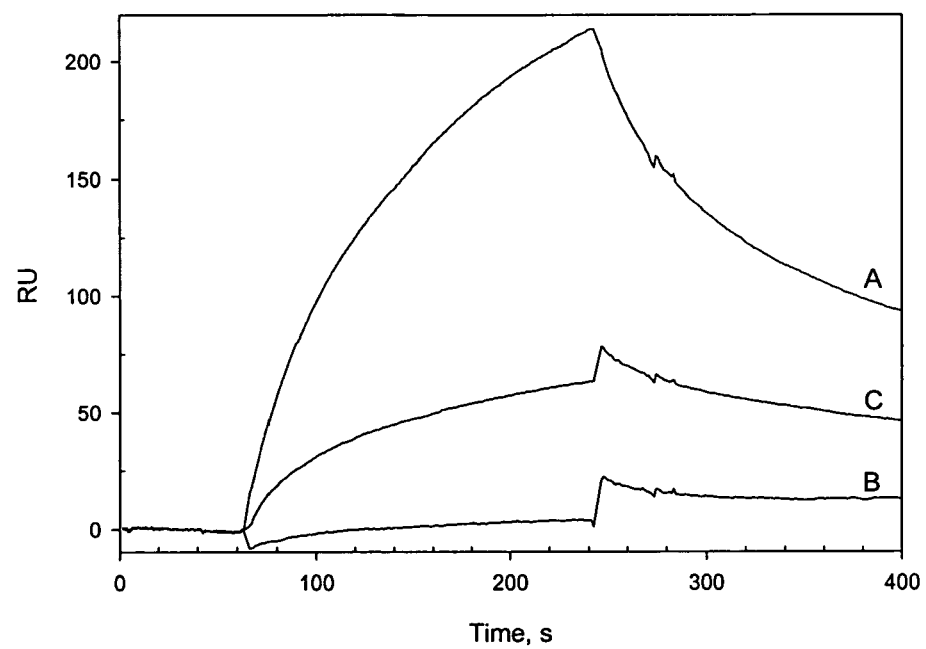

SEQUENCE LISTING

```
<160> NUMBER OF SEQ ID NOS: 9

<210> SEQ ID NO 1
<211> LENGTH: 340
<212> TYPE: PRT
<213> ORGANISM: Homo sapiens
```

<400> SEQUENCE: 1

```
Glu Arg Pro Lys Pro Pro Phe Pro Glu Leu Arg Lys Ala Val Pro Gly
 1               5                  10                  15

Asp Arg Thr Ala Gly Gly Pro Asp Ser Glu Leu Gln Pro Gln Asp
             20                  25                  30

Lys Val Ser Glu His Met Leu Arg Leu Tyr Asp Arg Tyr Ser Thr Val
             35                  40                  45

Gln Ala Ala Arg Thr Pro Gly Ser Leu Glu Gly Gly Ser Gln Pro Trp
         50                  55                  60

Arg Pro Arg Leu Leu Arg Glu Gly Asn Thr Val Arg Ser Phe Arg Ala
 65                  70                  75                  80

Ala Ala Ala Glu Thr Leu Glu Arg Lys Gly Leu Tyr Ile Phe Asn Leu
                 85                  90                  95

Thr Ser Leu Thr Lys Ser Glu Asn Ile Leu Ser Ala Thr Leu Tyr Phe
                100                 105                 110

Cys Ile Gly Glu Leu Gly Asn Ile Ser Leu Ser Cys Pro Val Ser Gly
            115                 120                 125

Gly Cys Ser His His Ala Gln Arg Lys His Ile Gln Ile Asp Leu Ser
130                 135                 140

Ala Trp Thr Leu Lys Phe Ser Arg Asn Gln Ser Gln Leu Leu Gly His
145                 150                 155                 160

Leu Ser Val Asp Met Ala Lys Ser His Arg Asp Ile Met Ser Trp Leu
                165                 170                 175

Ser Lys Asp Ile Thr Gln Phe Leu Arg Lys Ala Lys Glu Asn Glu Glu
            180                 185                 190

Phe Leu Ile Gly Phe Asn Ile Thr Ser Lys Gly Arg Gln Leu Pro Lys
            195                 200                 205

Arg Arg Leu Pro Phe Pro Glu Pro Tyr Ile Leu Val Tyr Ala Asn Asp
210                 215                 220

Ala Ala Ile Ser Glu Pro Glu Ser Val Val Ser Ser Leu Gln Gly His
225                 230                 235                 240

Arg Asn Phe Pro Thr Gly Thr Val Pro Lys Trp Asp Ser His Ile Arg
                245                 250                 255

Ala Ala Leu Ser Ile Glu Arg Arg Lys Lys Arg Ser Thr Gly Val Leu
            260                 265                 270

Leu Pro Leu Gln Asn Asn Glu Leu Pro Gly Ala Glu Tyr Gln Tyr Lys
        275                 280                 285

Lys Asp Glu Val Trp Glu Glu Arg Lys Pro Tyr Lys Thr Leu Gln Ala
290                 295                 300

Gln Ala Pro Glu Lys Ser Lys Asn Lys Lys Lys Gln Arg Lys Gly Pro
305                 310                 315                 320

His Arg Lys Ser Gln Thr Leu Gln Phe Asp Glu Gln Thr Leu Lys Lys
                325                 330                 335

Ala Arg Arg Lys
            340
```

<210> SEQ ID NO 2
<211> LENGTH: 335
<212> TYPE: PRT
<213> ORGANISM: Homo sapiens

<400> SEQUENCE: 2

```
Ser His Arg Ala Pro Ala Trp Ser Ala Leu Pro Ala Ala Ala Asp Gly
 1               5                  10                  15
```

```
Leu Gln Gly Asp Arg Asp Leu Gln Arg His Pro Gly Asp Ala Ala Ala
             20                  25                  30

Thr Leu Gly Pro Ser Ala Gln Asp Met Val Ala Val His Met His Arg
         35                  40                  45

Leu Tyr Glu Lys Tyr Ser Arg Gln Gly Ala Arg Pro Gly Gly Gly Asn
     50                  55                  60

Thr Val Arg Ser Phe Arg Ala Arg Leu Glu Val Val Asp Gln Lys Ala
 65                  70                  75                  80

Val Tyr Phe Phe Asn Leu Thr Ser Met Gln Asp Ser Glu Met Ile Leu
                 85                  90                  95

Thr Ala Thr Phe His Phe Tyr Ser Glu Pro Pro Arg Trp Pro Arg Ala
            100                 105                 110

Leu Glu Val Leu Cys Lys Pro Arg Ala Lys Asn Ala Ser Gly Arg Pro
        115                 120                 125

Leu Pro Leu Gly Pro Pro Thr Arg Gln His Leu Leu Phe Arg Ser Leu
130                 135                 140

Ser Gln Asn Thr Ala Thr Gln Gly Leu Leu Arg Gly Ala Met Ala Leu
145                 150                 155                 160

Ala Pro Pro Pro Arg Gly Leu Trp Gln Ala Lys Asp Ile Ser Pro Ile
                165                 170                 175

Val Lys Ala Ala Arg Arg Asp Gly Glu Leu Leu Leu Ser Ala Gln Leu
            180                 185                 190

Asp Ser Glu Glu Arg Asp Pro Gly Val Pro Arg Pro Ser Pro Tyr Ala
        195                 200                 205

Pro Tyr Ile Leu Val Tyr Ala Asn Asp Leu Ala Ile Ser Glu Pro Asn
    210                 215                 220

Ser Val Ala Val Thr Leu Gln Arg Tyr Asp Pro Phe Pro Ala Gly Asp
225                 230                 235                 240

Pro Glu Pro Arg Ala Ala Pro Asn Asn Ser Ala Asp Pro Arg Val Arg
                245                 250                 255

Arg Ala Ala Gln Ala Thr Gly Pro Leu Gln Asp Asn Glu Leu Pro Gly
            260                 265                 270

Leu Asp Glu Arg Pro Pro Arg Ala His Ala Gln His Phe His Lys His
        275                 280                 285

Gln Leu Trp Pro Ser Pro Phe Arg Ala Leu Lys Pro Arg Pro Gly Arg
    290                 295                 300

Lys Asp Arg Arg Lys Lys Gly Gln Glu Val Phe Met Ala Ala Ser Gln
305                 310                 315                 320

Val Leu Asp Phe Asp Glu Lys Thr Met Gln Lys Ala Arg Arg Lys
                325                 330                 335

<210> SEQ ID NO 3
<211> LENGTH: 472
<212> TYPE: PRT
<213> ORGANISM: Homo sapiens

<400> SEQUENCE: 3

Met Ala Gly Ala Ser Arg Leu Leu Phe Leu Trp Leu Gly Cys Phe Cys
  1               5                  10                  15

Val Ser Leu Ala Gln Gly Glu Arg Pro Lys Pro Pro Phe Pro Glu Leu
             20                  25                  30

Arg Lys Ala Val Pro Gly Asp Arg Thr Ala Gly Gly Gly Pro Asp Ser
         35                  40                  45

Glu Leu Gln Pro Gln Asp Lys Val Ser Glu His Met Leu Arg Leu Tyr
     50                  55                  60
```

-continued

```
Asp Arg Tyr Ser Thr Val Gln Ala Ala Arg Thr Pro Gly Ser Leu Glu
 65          70                  75                  80

Gly Gly Ser Gln Pro Trp Arg Pro Arg Leu Leu Arg Glu Gly Asn Thr
             85                  90                  95

Val Arg Ser Phe Arg Ala Ala Ala Glu Thr Leu Glu Arg Lys Gly
                100                 105                 110

Leu Tyr Ile Phe Asn Leu Thr Ser Leu Thr Lys Ser Glu Asn Ile Leu
                115                 120                 125

Ser Ala Thr Leu Tyr Phe Cys Ile Gly Glu Leu Gly Asn Ile Ser Leu
    130                 135                 140

Ser Cys Pro Val Ser Gly Cys Ser His His Ala Gln Arg Lys His
145             150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
            195                 200                 205

Ala Lys Glu Asn Glu Glu Phe Leu Ile Gly Phe Asn Ile Thr Ser Lys
    210                 215                 220

Gly Arg Gln Leu Pro Lys Arg Leu Pro Phe Pro Glu Pro Tyr Ile
225             230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
            275                 280                 285

Arg Ser Thr Gly Val Leu Leu Pro Leu Gln Asn Asn Glu Leu Pro Gly
    290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
            355                 360                 365

Asn Cys Ala Arg Arg Tyr Leu Lys Val Asp Phe Ala Asp Ile Gly Trp
    370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
                420                 425                 430

Pro Glu Pro Cys Cys Val Pro Glu Lys Met Ser Ser Leu Ser Ile Leu
            435                 440                 445

Phe Phe Asp Glu Asn Lys Asn Val Val Leu Lys Val Tyr Pro Asn Met
    450                 455                 460

Thr Val Glu Ser Cys Ala Cys Arg
465             470
```

-continued

```
<210> SEQ ID NO 4
<211> LENGTH: 478
<212> TYPE: PRT
<213> ORGANISM: Homo sapiens

<400> SEQUENCE: 4
```

| | | | | | | | | | | | | | | | |
|---|---|---|---|---|---|---|---|---|---|---|---|---|---|---|---|
| Met | Ala | His | Val | Pro | Ala | Arg | Thr | Ser | Pro | Gly | Pro | Gln | Leu | | |
| 1 | | | | 5 | | | | | 10 | | | | 15 | | |
| Leu | Leu | Leu | Leu | Leu | Pro | Leu | Phe | Leu | Leu | Leu | Arg | Asp | Val | Ala | |
| | | | 20 | | | | | 25 | | | | 30 | | | |
| Gly | Ser | His | Arg | Ala | Pro | Ala | Trp | Ser | Ala | Leu | Pro | Ala | Ala | Ala | Asp |
| | | 35 | | | | | 40 | | | | | 45 | | | |
| Gly | Leu | Gln | Gly | Asp | Arg | Asp | Leu | Gln | Arg | His | Pro | Gly | Asp | Ala | Ala |
| | 50 | | | | | 55 | | | | | 60 | | | | |
| Ala | Thr | Leu | Gly | Pro | Ser | Ala | Gln | Asp | Met | Val | Ala | Val | His | Met | His |
| 65 | | | | | 70 | | | | | 75 | | | | | 80 |
| Arg | Leu | Tyr | Glu | Lys | Tyr | Ser | Arg | Gln | Gly | Ala | Arg | Pro | Gly | Gly | Gly |
| | | | | 85 | | | | | 90 | | | | | 95 | |
| Asn | Thr | Val | Arg | Ser | Phe | Arg | Ala | Arg | Leu | Glu | Val | Val | Asp | Gln | Lys |
| | | | 100 | | | | | 105 | | | | | 110 | | |
| Ala | Val | Tyr | Phe | Phe | Asn | Leu | Thr | Ser | Met | Gln | Asp | Ser | Glu | Met | Ile |
| | | | 115 | | | | | 120 | | | | | 125 | | |
| Leu | Thr | Ala | Thr | Phe | His | Phe | Tyr | Ser | Glu | Pro | Pro | Arg | Trp | Pro | Arg |
| 130 | | | | | 135 | | | | | 140 | | | | | |
| Ala | Leu | Glu | Val | Leu | Cys | Lys | Pro | Arg | Ala | Lys | Asn | Ala | Ser | Gly | Arg |
| 145 | | | | | 150 | | | | | 155 | | | | | 160 |
| Pro | Leu | Pro | Leu | Gly | Pro | Pro | Thr | Arg | Gln | His | Leu | Leu | Phe | Arg | Ser |
| | | | | 165 | | | | | 170 | | | | | 175 | |
| Leu | Ser | Gln | Asn | Thr | Ala | Thr | Gln | Gly | Leu | Leu | Arg | Gly | Ala | Met | Ala |
| | | | 180 | | | | | 185 | | | | | 190 | | |
| Leu | Ala | Pro | Pro | Pro | Arg | Gly | Leu | Trp | Gln | Ala | Lys | Asp | Ile | Ser | Pro |
| | | | 195 | | | | | 200 | | | | | 205 | | |
| Ile | Val | Lys | Ala | Ala | Arg | Arg | Asp | Gly | Glu | Leu | Leu | Leu | Ser | Ala | Gln |
| | 210 | | | | | 215 | | | | | 220 | | | | |
| Leu | Asp | Ser | Glu | Glu | Arg | Asp | Pro | Gly | Val | Pro | Arg | Pro | Ser | Pro | Tyr |
| 225 | | | | | 230 | | | | | 235 | | | | | 240 |
| Ala | Pro | Tyr | Ile | Leu | Val | Tyr | Ala | Asn | Asp | Leu | Ala | Ile | Ser | Glu | Pro |
| | | | | 245 | | | | | 250 | | | | | 255 | |
| Asn | Ser | Val | Ala | Val | Thr | Leu | Gln | Arg | Tyr | Asp | Pro | Phe | Pro | Ala | Gly |
| | | | 260 | | | | | 265 | | | | | 270 | | |
| Asp | Pro | Glu | Pro | Arg | Ala | Ala | Pro | Asn | Asn | Ser | Ala | Asp | Pro | Arg | Val |
| | | | 275 | | | | | 280 | | | | | 285 | | |
| Arg | Arg | Ala | Ala | Gln | Ala | Thr | Gly | Pro | Leu | Gln | Asp | Asn | Glu | Leu | Pro |
| | 290 | | | | | 295 | | | | | 300 | | | | |
| Gly | Leu | Asp | Glu | Arg | Pro | Pro | Arg | Ala | His | Ala | Gln | His | Phe | His | Lys |
| 305 | | | | | 310 | | | | | 315 | | | | | 320 |
| His | Gln | Leu | Trp | Pro | Ser | Pro | Phe | Arg | Ala | Leu | Lys | Pro | Arg | Pro | Gly |
| | | | | 325 | | | | | 330 | | | | | 335 | |
| Arg | Lys | Asp | Arg | Arg | Lys | Lys | Gly | Gln | Glu | Val | Phe | Met | Ala | Ala | Ser |
| | | | 340 | | | | | 345 | | | | | 350 | | |
| Gln | Val | Leu | Asp | Phe | Asp | Glu | Lys | Thr | Met | Gln | Lys | Ala | Arg | Arg | Lys |
| | | | 355 | | | | | 360 | | | | | 365 | | |
| Gln | Trp | Asp | Glu | Pro | Arg | Val | Cys | Ser | Arg | Arg | Tyr | Leu | Lys | Val | Asp |
| | 370 | | | | | 375 | | | | | 380 | | | | |

```
Phe Ala Asp Ile Gly Trp Asn Glu Trp Ile Ile Ser Pro Lys Ser Phe
385                 390                 395                 400

Asp Ala Tyr Tyr Cys Ala Gly Ala Cys Glu Phe Pro Met Pro Lys Ile
            405                 410                 415

Val Arg Pro Ser Asn His Ala Thr Ile Gln Ser Ile Val Arg Ala Val
        420                 425                 430

Gly Ile Ile Pro Gly Ile Pro Glu Pro Cys Cys Val Pro Asp Lys Met
            435                 440                 445

Asn Ser Leu Gly Val Leu Phe Leu Asp Glu Asn Arg Asn Val Val Leu
        450                 455                 460

Lys Val Tyr Pro Asn Met Ser Val Asp Thr Cys Ala Cys Arg
465                 470                 475

<210> SEQ ID NO 5
<211> LENGTH: 1020
<212> TYPE: DNA
<213> ORGANISM: Homo sapiens

<400> SEQUENCE: 5
gagagaccga agccaccttt cccggagctc cgcaaagctg tgccaggtga ccgcacggca      60
ggtggtggcc cggactccga gctgcagccg caagacaagg tctctgaaca catgctgcgg     120
ctctatgaca ggtacagcac ggtccaggcg gcccggacac cgggctccct ggagggaggc     180
tcgcagccct ggcgccctcg gctcctgcgc gaaggcaaca cggttcgcag ctttcgggcg     240
gcagcagcag aaactcttga agaaaaagga ctgtatatct tcaatctgac atcgctaacc     300
aagtctgaaa acattttgtc tgccacactg tatttctgta ttggagagct aggaaacatc     360
agcctgagtt gtccagtgtc tggaggatgc tcccatcatg ctcagaggaa acacattcag     420
attgatcttt ctgcatggac cctcaaattc agcagaaacc aaagtcaact ccttggccat     480
ctgtcagtgg atatggccaa atctcatcga gatattatgt cctggctgtc taaagatatc     540
actcaattct tgaggaaggc caaagaaaat gaagagttcc tcataggatt aacattacg     600 tccaagggac gccagctgcc aaagaggagg ttaccttttc agagcctta tatcttggta     660 tatgccaatg atgccgccat ttctgagcca gaaagtgtgg tatcaagctt acaggacac     720 cggaatttt ccactggaac tgttcccaaa tgggatagcc acatcagagc tgcccttttcc     780 attgagcgga ggaagaagcg ctctactggg gtcttgctgc ctctgcagaa caacgagctt     840
cctggggcag aataccagta taaaaaggat gaggtgtggg aggagagaaa gccttacaag     900
acccttcagg ctcaggcccc tgaaaagagt aagaataaaa agaaacagag aaagggcct     960 catcggaaga gccagacgct ccaatttgat gagcagaccc tgaaaaaggc aaggagaaag    1020

<210> SEQ ID NO 6
<211> LENGTH: 1005
<212> TYPE: DNA
<213> ORGANISM: Homo sapiens

<400> SEQUENCE: 6
agccacaggg cccccgcctg gtccgcactg cccgcggccg ccgacggcct gcaggggggac      60 agggatctcc agcggcaccc tggggacgcg gccgccacgt gggcccccag cgccaggac     120 atggtcgctg tccacatgca caggctctat gagaagtaca gccggcaggg gcgcgggccg     180 ggaggggca acacggtccg cagcttcagg gccaggctgg aagtggtcga ccagaaggcc     240
gtgtatttct tcaacctgac ttccatgcaa gactcggaaa tgatccttac ggccactttc     300
```

```
cacttctact cagagccgcc tcggtggcct cgagcgctcg aggtgctatg caagccgcgg    360
gccaagaacg cttcaggccg cccgctgccc ctgggcccgc ccacacgcca gcacctgctc    420
ttccgcagcc tctcgcagaa cacgccaca cagggctac tccgcggggc catggccctg      480
gcgcccccac cgcgcggcct gtggcaggcc aaggacatct cccccatcgt caaggcggcc    540
cgccgggatg gcgagctgct cctctccgcc cagctggatt ctgaggagag ggacccgggg    600
gtgccccggc ccagccccta tgcgccctac atcctagtct atgccaacga tctggccatc    660
tcggagccca acagcgtggc agtgacgctg cagagatacg ccccttccc tgccggagac     720 cccgagcccc gcgcagcccc caacaactca gcggaccccc gcgtgcgccg agccgcgcag    780
gccactgggc ccctccagga acgagctg ccggggctgg atgagaggcc gccgcgcgcc      840
cacgcacagc acttccacaa gcaccagctg tgcccagcc ccttccgggc gctgaaaccc     900
cggccagggc gcaaagaccg caggaagaag ggccaggagg tgttcatggc cgcctcgcag    960
gtgctggact tgacgagaa gacgatgcag aaagcccgga ggaag                     1005

<210> SEQ ID NO 7
<211> LENGTH: 1419
<212> TYPE: DNA
<213> ORGANISM: Homo sapiens

<400> SEQUENCE: 7
atggctgggg cgagcaggct gctctttctg tggctgggct gcttctgcgt gagcctggcg     60
cagggagaga gaccgaagcc acctttcccg gagctccgca agctgtgcc aggtgaccgc    120 acggcaggtg gtggcccgga ctccgagctg cagccgcaag acaaggtctc tgaacacatg    180
ctgcggctct atgacaggta cagcacggtc caggcggccc ggacaccggg ctccctggag    240
ggaggctcgc agccctggcg ccctcggctc ctgcgcgaag gcaacacggt tcgcagcttt    300
cgggcggcag cagcagaaac tcttgaaaga aaaggactgt atatcttcaa tctgacatcg    360
ctaaccaagt ctgaaaacat tttgtctgcc acactgtatt tctgtattgg agagctagga    420
aacatcagcc tgagttgtcc agtgtctgga ggatgctccc atcatgctca gaggaaacac    480
attcagattg atctttctgc atggacctc aaattcagca gaaaccaaag tcaactcctt    540
ggccatctgt cagtggatat ggccaaatct catcgagata ttatgtcctg gctgtctaaa    600
gatatcactc aattcttgag gaaggccaaa gaaaatgaag agttcctcat aggatttaac    660
attacgtcca agggacgcca gctgccaaag aggaggttac cttttccaga gccttatatc    720
ttggtatatg ccaatgatgc cgccatttct gagccagaaa gtgtgggtatc aagcttacag    780 ggacaccgga ttttccccac tggaactgtt cccaaatggg atagccacat cagagctgcc    840
ctttccattg agcggaggaa gaagcgctct actggggtct gctgcctct gcagaacaac    900 gagcttcctg ggcagaata ccagtataaa aaggatgagg tgtgggagga gagaaagcct    960
tacaagaccc ttcaggctca ggcccctgaa aagagtaaga ataaaaagaa acagagaaag   1020
gggcctcatc ggaagagcca gacgctccaa tttgatgagc agaccctgaa aaaggcaagg   1080
agaaagcagt ggattgaacc tcggaattgc gccaggagat acctcaaggt agactttgca   1140
gatattggct ggagtgaatg gattatctcc cccaagtcct tgatgcctat ttattgctct   1200
ggagcatgcc agttccccat gccaaagtct ttgaagccat caaatcatgc taccatccag   1260
agtatagtga gagctgtggg ggtcgttcct gggattcctg agccttgctg tgtaccagaa   1320
aagatgtcct cactcagtat tttattcttt gatgaaaata agaatgtagt gcttaaagta   1380
taccctaaca tgacagtaga gtcttgcgct tgcagataa                          1419
```

<210> SEQ ID NO 8
<211> LENGTH: 1437
<212> TYPE: DNA
<213> ORGANISM: Homo sapiens

<400> SEQUENCE: 8

| | | | | | |
|---|---|---|---|---|---|
| atggctcatg | tccccgctcg | gaccagcccg | ggacccgggc | cccagctgct | gctgctgctg | 60 |
| ctgccgttgt | ttctgctgtt | gctccgggat | gtggccggca | gccacagggc | cccgcctgg | 120 |
| tccgcactgc | ccgcggccgc | cgacggcctg | caggggaca | gggatctcca | gcggcaccct | 180 |
| ggggacgcgg | ccgccacgtt | gggccccagc | gcccaggaca | tggtcgctgt | ccacatgcac | 240 |
| aggctctatg | agaagtacag | ccggcagggc | gcgcggccgg | gaggggggcaa | cacggtccgc | 300 |
| agcttcaggg | ccaggctgga | agtggtcgac | cagaaggccg | tgtatttctt | caacctgact | 360 |
| tccatgcaag | actcggaaat | gatccttacg | gccactttcc | acttctactc | agagccgcct | 420 |
| cggtggcctc | gagcgctcga | ggtgctatgc | aagccgcggg | ccaagaacgc | ttcaggccgc | 480 |
| ccgctgcccc | tgggcccgcc | acacgccag | cacctgctct | ccgcagcct | ctcgcagaac | 540 |
| acggccacac | aggggctact | ccgcggggcc | atggccctgg | cgcccccacc | gcgcggcctg | 600 |
| tggcaggcca | aggacatctc | ccccatcgtc | aaggcggccc | gccgggatgg | cgagctgctc | 660 |
| ctctccgccc | agctggattc | tgaggagagg | gaccgggggg | tgccccggcc | cagcccctat | 720 |
| gcgccctaca | tcctagtcta | tgccaacgat | ctggccatct | cggagcccaa | cagcgtggca | 780 |
| gtgacgctgc | agagatacga | ccccttccct | gccgagacc | ccgagccccg | cgcagccccc | 840 |
| aacaactcag | cggaccccg | cgtgcgccga | gccgcgcagg | ccactgggcc | cctccaggac | 900 |
| aacgagctgc | cggggctgga | tgagaggccg | ccgcgcgccc | acgcacagca | cttccacaag | 960 |
| caccagctgt | ggcccagccc | cttccgggcg | ctgaaacccc | ggccagggcg | caaagaccgc | 1020 |
| aggaagaagg | gccaggaggt | gttcatggcc | gcctcgcagg | tgctggactt | tgacgagaag | 1080 |
| acgatgcaga | aagcccggag | gaagcagtgg | gatgagccga | gggtgtgctc | ccggaggtac | 1140 |
| ctgaaggtgg | acttcgcaga | catcggctgg | aatgaatgga | taatctcacc | gaaatctttt | 1200 |
| gatgcctact | actgcgcggg | agcatgtgag | ttccccatgc | ctaagatcgt | tcgtccatcc | 1260 |
| aaccatgcca | ccatccagag | cattgtcagg | gctgtgggca | tcatccctgg | catcccagag | 1320 |
| ccctgctgtg | ttcccgataa | gatgaactcc | cttggggtcc | tcttcctgga | tgagaatcgg | 1380 |
| aatgtggttc | tgaaggtgta | ccccaacatg | tccgtggaca | cctgtgcctg | ccggtga | 1437 |

<210> SEQ ID NO 9
<211> LENGTH: 225
<212> TYPE: PRT
<213> ORGANISM: Homo sapiens

<400> SEQUENCE: 9

Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

-continued

```
Val Ser Val Leu Thr Val Leu His Gln Asp Trp Leu Asn Gly Lys Glu
                 85              90                  95
Tyr Lys Cys Lys Val Ser Asn Lys Ala Leu Pro Val Pro Ile Glu Lys
            100             105             110
Thr Ile Ser Lys Ala Lys Gly Gln Pro Arg Glu Pro Gln Val Tyr Thr
            115             120             125
Leu Pro Pro Ser Arg Glu Glu Met Thr Lys Asn Gln Val Ser Leu Thr
        130             135             140
Cys Leu Val Lys Gly Phe Tyr Pro Ser Asp Ile Ala Val Glu Trp Glu
145             150             155             160
Ser Asn Gly Gln Pro Glu Asn Asn Tyr Lys Thr Thr Pro Pro Val Leu
            165             170             175
Asp Ser Asp Gly Pro Phe Phe Leu Tyr Ser Lys Leu Thr Val Asp Lys
            180             185             190
Ser Arg Trp Gln Gln Gly Asn Val Phe Ser Cys Ser Val Met His Glu
        195             200             205
Ala Leu His Asn His Tyr Thr Gln Lys Ser Leu Ser Leu Ser Pro Gly
        210             215             220
Lys
225
```

BMP-3 PROPEPTIDES AND RELATED METHODS

RELATED APPLICATIONS

This application claims the benefit of the filing date of U.S. Provisional Application No. 60/557,100, filed Mar. 26, 2004, the specification of which is incorporated by reference herein in its entirety.

BACKGROUND OF THE INVENTION

Bone morphogenetic proteins (BMPs) are members of the transforming growth factor-β superfamily. Many BMPs are produced in bone and modulate osteogenic activity, which suggests that these proteins are involved in building bone mass. Members of the BMP family include BMP-2 and BMP-3. BMP-2 has been implicated in multiple functions associated with bone formation and growth. For example, the protein induces differentiation of osteoprogenitor cells into osteoblasts, and to enhance healing of bone fractures.

BMP-3 is also termed BMP-3A. A closely related protein termed BMP-3B is also known as growth and differentiation factor 10 (GDF-10). These two proteins show great amino acid sequence similarity in the region corresponding to the mature (fully processed) form, corresponding the C-terminal portion of the unprocessed protein. The differences between the sequences of BMP-3A and BMP-3B are located mainly outside the mature peptide regions, with the propeptides showing significant sequence divergence. BMP-3A was originally purified from bone as osteogenin and is particularly abundant in demineralized bone. Recombinant BMP-3A showed no osteogenic activity and instead was reported to antagonize the osteogenic activity of BMP-2. Zhu et al., Chin J Biotechnol. 1999; 15(3): 153-8. This result was supported by an observed increase in bone density and volume in a BMP-3A −/− knock-out mouse. Daluiski et al., Nat Genet. 2001 January;27(1):84-8.

In view of the above findings, a need exists for a manner of regulating BMP-3A activity, particularly in individuals who are in need of increased bone mass or increased bone growth, such as individuals with osteoporosis or bone fractures.

SUMMARY OF THE INVENTION

In certain aspects, the present disclosure provides BMP-3 propeptides. As disclosed herein, BMP-3 propeptides bind to mature BMP-3 and competitively inhibit binding to Type II receptor. Accordingly, BMP-3 propeptides may be used to inhibit BMP-3—Type II receptor mediated signaling. BMP-3 propeptides may be used for treating bone disorders, and particularly those disorders where increases in bone density or volume are desirable, as in the treatment of osteoporosis and bone fractures. Additionally, such propeptides may inhibit other members of the BMP family and will be useful in the treatment of additional disorders. Likewise, the mature BMP-3A and 3B polypeptides may participate in other biological processes, and a BMP-3 propeptide disclosed herein may be used to antagonize BMP-3A and 3B in any BMP-3 related process. Examples of BMP-3 propeptides include the propeptides of BMP-3A and BMP-3B, as well as any functional variants thereof. In certain cases, the BMP-3 propeptide inhibits the interaction between a mature BMP-3 polypeptide and an ActRIIa polypeptide. In other cases, the BMP-3 propeptide inhibits any signaling mediated by interaction between a mature BMP-3 polypeptide and an ActRIIa polypeptide. Optionally, a BMP-3 propeptide derepresses or increases bone growth. Additionally, the disclosure provides antibodies that bind a mature BMP-3 peptide in a manner similar to a BMP-3 propeptide. Such antibodies may also be used to treat bone disorders or other BMP-3 related disorders.

In certain aspects, the disclosure provides pharmaceutical preparations for promoting bone growth and/or inhibiting bone loss. Such preparations may comprise a BMP-3 propeptide that binds to a mature BMP-3 polypeptide and a pharmaceutically acceptable carrier. In certain cases, the BMP-3 propeptide inhibits the interaction between a mature BMP-3 polypeptide and an ActRIIa polypeptide. In other cases, the BMP-3 propeptide inhibits any signaling mediated by interaction between a mature BMP-3 polypeptide and an ActRIIa polypeptide. Optionally, a BMP-3 propeptide derepresses or increases bone growth. Preferably the BMP-3 propeptide binds to a mature BMP-3 with a KD less than 1 micromolar or less than 100, 10 or 1 nanomolar. A BMP-3 propeptide for use in such a preparation may be any of those disclosed herein, such as a polypeptide having an amino acid sequence of SEQ ID NO:1 or 2 or having an amino acid sequence that is at least 80%, 85%, 90%, 95%, 97% or 99% identical to an amino acid sequence of SEQ ID NO:1 or 2. A BMP-3 propeptide may include a functional fragment of a natural BMP-3 propeptide, such as one comprising at least 10, 20 or 30 amino acids of SEQ ID NO:1 or 2. A BMP-3 propeptide will generally not contain a full-length or functional portion of a mature BMP-3 polypeptide, and preferably a BMP-3 propeptide will include no more than 50, 40, 30, 20, 10 or 5 amino acids of a mature portion of a BMP-3 polypeptide. A BMP-3 propeptide may include an alteration in the amino acid sequence relative to a naturally occurring BMP-3 propeptide. The alteration in the amino acid sequence may alter glycosylation of the polypeptide when produced in a mammalian, insect or other eukaryotic cell or alter proteolytic cleavage of the polypeptide relative to the naturally occurring BMP-3 polypeptide. A BMP-3 propeptide may be a fusion protein that has, as one domain, a BMP-3 propeptide (including any of the various truncations or variations described herein) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A BMP-3 propeptide fusion protein may include an immunoglobulin Fc domain or a serum albumin. A fusion protein may include a purification subsequence, such as an epitope tag, a FLAG tag, a polyhistidine sequence, and a GST fusion. Optionally, a BMP-3 propeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as: a compound that inhibits bone resorption, a compound that stimulates bone formation, and/or a compound that increases bone mineral density. For example, the preparation may include a bisphosphonate. Preferably, a pharmaceutical preparation is substantially pyrogen free. Preferably, a pharmaceutical composition comprising a BMP-3 propeptide will not include, as a separate component, an active mature BMP-3 protein.

In certain aspects, the disclosure provides packaged pharmaceuticals comprising a pharmaceutical preparation described herein and labeled for use in promoting increased bone density or growth or diminishing or preventing bone loss or demineralization in a human or non-human patient.

In certain aspects, the disclosure provides nucleic acids encoding a BMP-3 propeptide that do not encode a complete, translatable mature portion of a BMP-3. An isolated polynucleotide may comprise a coding sequence for a BMP-3 propeptide, such as described above. An isolated nucleic acid may include a sequence coding for a BMP-3 propeptide and a sequence that would code for part or all of a mature portion, but for a stop codon positioned within the mature portion or positioned between the propeptide and the mature portion. For example, an isolated polynucleotide may comprise a polynucleotide sequence coding for a polypeptide selected from the group consisting of SEQ ID NO:7 and 8, said isolated polynucleotide further comprising a transcription termination codon at least three hundred nucleotides before the 3'-terminus. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a BMP-3 propeptide. Such a method may include expressing any of the propeptide encoding nucleic acids disclosed herein in a suitable cell, such as a Chinese hamster ovary (CHO) cell. Such a method may comprise: a) culturing a cell under conditions suitable for expression of the propeptide, wherein said cell is transformed with a BMP-3 propeptide expression construct; and b) recovering the propeptide so expressed.

In certain aspects, the disclosure provides methods for treating a subject having a disorder associated with insufficient bone mineral density, bone loss, bone damage or insufficient bone growth, the method comprising administering to the subject an effective amount of a BMP-3 propeptide. The BMP-3 propeptide may be any of those disclosed herein. The subject may suffer from, for example, lower than normal bone mineral density, osteoporosis or a fracture. A method may include co-administration with an additional agent, such as a bisphosphonate. In certain embodiments, the disclosure provides methods for increasing bone density and/or bone volume in a subject, the method comprising administering a BMP-3 propeptide disclosed herein.

In further aspects, the disclosure provides methods for identifying an agent that increases bone density and/or bone volume. A method may comprise: a) identifying a test agent that binds a mature BMP-3 polypeptide competitively with a BMP-3 propeptide; and b) evaluating the effect of the agent on bone growth. A test agent may be, for example, a variant BMP-3 propeptide, an antibody, or a small molecule.

BRIEF DESCRIPTION OF THE DRAWINGS

FIG. 1 shows a BMP-3A propeptide amino acid sequence (SEQ ID NO: 1).

FIG. 2 shows a BMP-3B/GDF-10 propeptide amino acid sequence (SEQ ID NO: 2).

FIG. 3 shows a BMP-3A precursor amino acid sequence (SEQ ID NO: 3). The signal peptide (residues 1-22) is underlined; the prodomain (residues 23-362) is in bold, also referred to as SEQ ID NO: 1; and the mature protein (residues 363-472) is shaded. The potential N-linked glycosylation sites are boxed.

FIG. 4 shows a BMP-3B/GDF-10 precursor amino acid sequence (SEQ ID NO: 4). The signal peptide (residues 1-33) is underlined; the prodomain (residues 34-368) is in bold, also referred to as SEQ ID NO: 2; and the mature protein (residues 369-478) is shaded. The potential N-linked glycosylation sites are boxed.

FIG. 5 shows a nucleic acid sequence encoding a BMP-3A propeptide, designed as SEQ ID NO: 5.

FIG. 6 shows a nucleic acid sequence encoding a BMP-3B propeptide, designed as SEQ ID NO: 6.

FIG. 7 shows a nucleic acid sequence encoding the BMP-3A precursor protein, designed as SEQ ID NO: 7.

FIG. 8 shows a nucleic acid sequence encoding the BMP-3B precursor protein, designed as SEQ ID NO: 8.

FIG. 9 shows a human Fc amino acid sequence. Certain optional mutations are shown in red.

FIG. 10 shows BMP3A propeptide—Murine IgG2a peptide Fc fusion protein ("BMP3 pro-MuIg2a") purified using Protein A affinity step. Lane 1 indicates molecular weight markers, while Lane 2 shows the BMP3-Pro-MuFc fusion purified from conditioned media of cells expressing BMP3 pro-MuIgG2a by Protein A affinity purification.

FIG. 11 shows that BMP3 pro-MuIgG2a peptide binds mature BMP-3. Lane 1: Molecular Weight Markers. Lane 2: Control-incubation of protein A beads with conditioned media from 293 cells transfected with vector alone and mature BMP-3. Lane 3: Conditioned media from HEK293 cell expressing BMP3 pro-MuIgG2a-peptide incubated with BMP-3 and Protein A.

FIG. 12 shows binding of purified BMP3 pro-MuIgG2a to mature BMP-3 using BiaCore CM5 chip analysis. Purified BMP3 pro-MuIgG2a was coupled onto a BiaCore CM5 chip using the amine coupling procedure. Panel A: Mature BMP-3 was flowed over the chip. Panel B: Control experiment showing that BSA does not bind to BMP3 pro-MuIgG2a Fc.

FIG. 13 shows that mature BMP-3 binds to Activin Receptor IIa (ActRIIa) and BMP3 pro-MuIgG2a Fc competes with ActRIIa binding to BMP-3. ActRIIa was immobilized on a BiaCore CM5 chip using standard amine coupling procedure. Trace A: Mature BMP-3 (200 µg/ml) was injected on the ActRIIa coupled chip. Trace B: BMP3 pro-MuIgG2a Fc (100 µg/ml) was injected onto the ActRIIa chip (no binding). Trace C: Mature BMP-3 (200 µg/ml) and BMP3 pro-MuIgG2a (100 µg/ml)) were premixed and injected onto the ActRIIa coupled chip.

DETAILED DESCRIPTION OF THE INVENTION

1. Overview

The present invention relates to Bone morphogenetic protein-3 (BMP-3) propeptides. As used herein, the term "BMP-3" refers to the family of bone morphogenetic proteins of the type 3, derived from any species. Reference to BMP-3 herein is understood to be a reference to any one of the currently identified forms, including BMP-3A (also known as BMP-3) and BMP-3B (also known as GDF-10), as appropriate from the context. The term "BMP-3" also includes polypeptides derived from the sequence of any known BMP-3 whose mature sequence is at least about 75% homologous with the sequence of a mature BMP-3, and preferably at least 80%, 85%, 90%, 95%, 97%, 99% or greater homology. Members of the BMP-3 family are generally encoded as a larger precursor, and members of the family share a region of high homology near the C-terminus, corresponding generally to the mature portion. For example, BMP-3B shares 82% amino acid identity with BMP-3A in the mature peptide (mature domain), but only 37% in the propeptide. Note that because the mature proteins share substantial homology, it is expected that the BMP-3A propeptide will bind to either mature protein.

A naturally occurring BMP-3 protein is generally encoded as a larger precursor that typically contains a signal sequence at its N-terminus followed by a dibasic amino acid cleavage site and a propeptide, followed by another dibasic amino acid cleavage site and a mature domain. Thus, as used herein, the term "propeptide" or "prodomain" is the portion that is N-terminal to the mature domain and C-terminal to the signal peptide. Optionally, a BMP-3 propeptide, after cleavage, reassociates with its mature peptide covalently or non-covalently, as in the case of insulin, relaxin, inhibin, activin, and TGF-β. The term "BMP-3 propeptide" is used to refer to polypeptides comprising any naturally occurring propeptide of a BMP-3 family member as well as any variants thereof (including mutants, fragments and peptidomimetic forms) that retain a useful activity. As used herein, BMP-3 propeptides include fragments, functional variants, and modified forms (e.g., peptidomimetic forms) of BMP-3 propeptides. A "BMP-3 propeptide" will not include a full-length mature BMP-3 domain, although a BMP-3 propeptide may include portions of the mature domain, particularly portions that are not fully functional. For example, a BMP-3 propeptide may contain fewer than 50, 40, 30, 20, 10 or 5 amino acids of its cognate mature domain. Functional variants of a BMP-3 propeptide may be characterized by, for example, binding to mature BMP-3 protein and/or the ability to competitively inhibit the binding of BMP-3 to a type II receptor, such as ActRIIa.

BMP-3A and BMP-3B together represent a unique subgroup of the BMP family. In osteoblasts, BMP-3A and 3B have been shown to antagonize the BMP-2 activity (Hino et al., 2004, Front Biosci., 9:1520-9; Daluiski et al, 2001, Nature Genetics, 27:84-88). BMP-2 is known to promote bone formation and mineralization; BMP-2 is reported to stimulate osteoblasts and is also reported to promote the production of osteoblasts from progenitor cells. While not wishing to be bound to any particular mechanism, it is expected that a BMP-3 propeptide promotes bone growth (meaning increased bone density, volume or other appropriate metric) by antagonizing the mature BMP-3, thus dis-inhibiting one or more BMP-2 functions. BMP-3 may also have independent effects, perhaps stimulating osteoclasts, and thus causing increased bone resorbtion. The sequences of BMP-3A and BMP-3B precursor proteins (i.e., signal peptide, propeptide, and mature peptide) are illustrated in FIG. 3 and FIG. 4, respectively.

As described in the working examples, Applicants have demonstrated that a BMP-3 propeptide (e.g., a BMP-3 Fc fusion protein) binds to mature BMP-3A and competes with mature BMP-3A for binding to the Activin Receptor IIa (ActRIIa). Accordingly, in certain embodiments, compositions and methods of the present invention are useful for inhibiting interaction between mature BMP-3A and ActRIIa. In further embodiments, compositions and methods of the present invention are useful for inhibiting any signaling mediated by interaction between mature BMP-3A and ActRIIa.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "bone loss" and "bone growth" are used herein to refer to changes (decreases or increases, respectively) in size or density of bone measured in any way, such as changes in bone volume, density or mineralization. For example, these characteristics may be assessed in terms of rates of loss or growth or in terms of snapshot (single time point) or equilibrium comparisons.

The disclosure may refer to the comparison of sequences to each other, including the comparison of wild-type sequence to one or more mutants/sequence variants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. BMP-3 Propeptides

In certain aspects, the invention relates to BMP-3 propeptides. Preferably, these fragments, functional variants, and modified forms have biological activities that are similar to or the same as that of their corresponding wild-type BMP-3 propeptides. For example, a BMP-3 propeptide of the invention binds to and inhibits a function of a mature BMP-3 protein. In certain cases, the BMP-3 propeptide inhibits the interaction between a mature BMP-3 polypeptide and an ActRIIa polypeptide. In other cases, the BMP-3 propeptide inhibits any signaling mediated by interaction between a mature BMP-3 polypeptide and an ActRIIa polypeptide. Optionally, a BMP-3 propeptide derepresses or increases bone growth.

Examples of BMP-3 propeptides include a BMP-3A propeptide (SEQ ID NO: 1) and a BMP-3B propeptide (SEQ ID NO: 2). Although the BMP-3A and 3B propeptides are only distantly similar in amino acid sequence, each binds to a mature polypeptide of similar sequence, and accordingly it is expected that BMP-3B propeptide binds BMP-3A and vice versa.

In one specific example, human BMP-3A cDNA (SEQ ID NO: 7, FIG. 7) encodes a 472-amino acid precursor protein (SEQ ID NO: 3, FIG. 3). Cleavage of the BMP-3A precursor protein at a putative polybasic proteolytic cleavage site (residues 357-362 of SEQ ID NO: 3) generates a mature BMP-3A protein consisting of 110 amino acids (FIG. 3) and a BMP-3A propeptide consisting of 340 amino acids (FIGS. 1 and 3, SEQ ID NO: 1). The BMP-3A propeptide contains potential glycosylation sites (FIG. 3). See, e.g., Wozney et al., 1988, Science. 242:1528-34.

In another specific example, human BMP-3B cDNA (SEQ ID NO: 8, FIG. 8) encodes a 478-amino acid precursor protein. Cleavage of the BMP-3B precursor protein at a putative polybasic proteolytic cleavage site (residues 364-368 of SEQ ID NO: 4) generates a mature BMP-3B protein consisting of 110 amino acids and a BMP-3B propeptide consisting of 335 amino acids (FIGS. 2 and 4, SEQ ID NO: 2). Both the BMP-3B propeptide and the BMP-3B mature peptide contain potential glycosylation sites (FIG. 4). See, e.g., Hino et al., 1996, Biochem. Biophys. Res. Commun. 223 (2), 304-310.

In certain embodiments, isolated fragments of the BMP-3 propeptides can be obtained by screening polypeptides recombinantly produced from the corresponding fragment of the nucleic acid encoding a BMP-3 propeptide (e.g., SEQ ID NO: 1 or 2). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function to stimulate bone growth, for example, as antagonists of the BMP-3 activity or as activator of BMP-2 activity.

In certain embodiments, a functional variant of the BMP-3 propeptides has an amino acid sequence that is at least 75% identical to an amino acid sequence as set forth in SEQ ID NO: 1 or 2. In certain cases, the functional variant has an amino acid sequence at least 80%, 85%, 90%, 95%, 97%, 98%, 99% or 100% identical to an amino acid sequence as set forth in SEQ ID NO: 1 or 2. Preferably such variants retain the ability to bind to mature BMP-3 and/or competitively inhibit the binding of BMP-3 to a type II receptor.

In certain embodiments, the present invention contemplates making functional variants by modifying the structure of a BMP-3 propeptide. Such modifications may be made, for example, for such purposes as enhancing therapeutic efficacy, or stability (e.g., ex vivo shelf life and resistance to proteolytic degradation in vivo). Such modified BMP-3 propeptides when designed to retain at least one activity of the naturally-occurring form of the BMP-3 propeptides, are considered functional equivalents of the naturally-occurring propeptides. Modified BMP-3 propeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a BMP-3 propeptide results in a functional homolog can be readily determined by assessing the ability of the variant propeptide to produce a response in cells in a fashion similar to the wild-type propeptide.

In certain embodiments, the present invention contemplates making mutations in the proteolytic cleavage site of the BMP-3 propeptide sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the BMP-3 propeptide sequences so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which are specifically recognized by appropriate cellular glycosylation enzymes. The alteration may also be made by the addition of, or substitution by, one or more serine or threonine residues to the sequence of the wild-type BMP-3 propeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a BMP-3 propeptide is by chemical or enzymatic coupling of glycosides to the BMP-3 propeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a BMP-3 propeptide may be accomplished chemically and/or enzymatically. Chemical deglycosylation may involve, for example, exposure of the BMP-3 propeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on BMP-3 propeptides can be achieved by the use of a variety of endo- and exo-glycosidases as described by Thotakura et al. (1987) Meth. Enzymol. 138:350. The nucleic acid and/or amino acid sequence of a propeptide may be adjusted, as appropriate, depending on the type of expression system used, as mammalian, yeast, insect and plant cells may all introduce differing glycosylation patterns that can be affected by the amino acid sequence of the peptide.

This disclosure further contemplates a method of generating mutants, particularly sets of combinatorial mutants of the BMP-3 propeptide, as well as truncation mutants; pools of combinatorial mutants are especially useful for identifying functional variant sequences. The purpose of screening such combinatorial libraries may be to generate, for example, BMP-3 propeptide variants which can act as either agonists or antagonist, or alternatively, which possess novel activities all together. A variety of screening assays are provided below, and such assays may be used to evaluate variants. For example, a BMP-3 propeptide variant may be screened for ability to bind to a mature BMP-3 polypeptide, or for the ability to prevent binding of a mature BMP-3 to a cell expressing a BMP-3 receptor, such as an ActRII. The activity of a BMP-3 may also be tested in a cell-based or in vivo assay. For example, the effect of a BMP-3 propeptide on the expression of genes involved in bone production in an osteoblast or precursor may be assessed. This may, as needed, be performed in the presence of recombinant BMP-3 and/or BMP-2, and cells may be transfected so as to produce any of BMP-2, BMP-3 and the subject BMP-3 propeptide variant. Likewise, a BMP-3 propeptide may be administered to a mouse or other animal, and one or more bone properties, such as density or volume may be assessed. The healing rate for bone fractures may also be evaluated.

Combinatorially-derived variants can be generated which have a selective potency relative to a naturally occurring BMP-3 propeptide. Such variant proteins, when expressed from recombinant DNA constructs, can be used in gene therapy protocols. Likewise, mutagenesis can give rise to variants which have intracellular half-lives dramatically different than the corresponding wild-type propeptide. For example, the altered protein can be rendered either more stable or less stable to proteolytic degradation or other cellular process which result in destruction of, or otherwise inactivation of a native BMP-3 propeptide. Such variants, and the genes which encode them, can be utilized to alter BMP-3 propeptide levels by modulating the half-life of the propeptide. For instance, a short half-life can give rise to more transient biological effects and, when part of an inducible expression system or scheduled dosing regimen, can allow tighter control of recombinant BMP-3 propeptide levels in the treated subject.

In a preferred embodiment, the combinatorial library is produced by way of a degenerate library of genes encoding a library of polypeptides which each include at least a portion of potential BMP-3 propeptide sequences. For instance, a mixture of synthetic oligonucleotides can be enzymatically ligated into gene sequences such that the degenerate set of potential BMP-3 propeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, BMP-3 propeptide variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218: 597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of BMP-3 propeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of BMP-3 propeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the BMP-3 propeptides of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the BMP-3 propeptides.

To illustrate, by employing scanning mutagenesis to map the amino acid residues of a BMP-3 propeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffinan et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the BMP-3 propeptides of the invention may further comprise post-translational modifications in addition to any that are naturally present in the propeptide. Such modifications include, but are not limited to, acetylation, carboxylation, glycosylation, phosphorylation, lipidation, and acylation. As a result, the modified BMP-3 propeptides may contain non-amino acid elements, such as polyethylene glycols, lipids, poly- or mono-saccharide, and phosphates. Effects of such non-amino acid elements on the functionality of a BMP-3 propeptide may be tested as described herein for other BMP-3 propeptide variants. When a BMP-3 propeptide is produced in cells by cleaving a nascent form of the BMP-3 protein, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the BMP-3 protein into a BMP-3 propeptide.

In certain aspects, functional variants or modified forms of the BMP-3 propeptides include fusion proteins having at least a portion of the BMP-3 propeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the BMP3 propeptide. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a BMP-3 propeptide is fused with a domain that stabilizes the propeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. In addition, Fc fusions tend to dimerize, providing a dimeric BMP-3 propeptide. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth).

It is understood that different elements of the fusion proteins may be arranged in any manner that is consistent with the desired functionality. For example, a BMP-3 propeptide may be placed C-terminal to a heterologous domain, or, alternatively, a heterologous domain may be placed C-terminal to a BMP-3 propeptide. The propeptide domain and the heterologous domain need not be adjacent in a fusion protein, and additional domains or amino acid sequences may be included C- or N-terminal to either domain or between the domains.

In certain embodiments, the BMP-3 propeptides of the present invention contain one or more modifications that are capable of stabilizing the BMP-3 propeptides. For example, such modifications enhance the in vitro half life of the propeptides, enhance circulatory half life of the propeptides or reducing proteolytic degradation of the propeptides. Such stabilizing modifications include, but are not limited to, fusion proteins (including, for example, fusion proteins comprising a BMP-3 propeptide and a stabilizer domain), modifications of a glycosylation site (including, for example, addition of a glycosylation site to a BMP-3 propeptide), and modifications of carbohydrate moiety (including, for example, removal of carbohydrate moieties from a BMP-3 propeptide). In the case of fusion proteins, a BMP-3 propeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol (PEG). PEG may be affixed to BMP-3 propeptides in a variety of sizes, ranging from 1000 D to 50,000 D or more molecular weight polymers. PEG polymers may be affixed to propeptides in a selective, residue specific manner, particularly when directed against the N-terminal amine or an engineered cysteine. PEG polymers may also be affixed in a relatively uncontrolled reaction, in which primary amines and/or sulfhydryl groups may be reacted. The stoichiometry may range from 1:1 (PEG: Propeptide) to 2:1 and higher.

In certain embodiments, the BMP-3 propeptide is fused with an immunoglobulin Fc domain. In a preferred embodiment, the Fc domain is an IgG1 Fc fragment. An IgG1 Fc fragment may include various alterations, including, for example, mutations that reduce binding to Fcγ Receptor and mutations that decreased binding to MHC class I-related Fc-receptor (FcRN). Examples of mutations include mutations in the an Fc portion at positions 265 (Asp to Ala), 322 (Lys to Ala), and 434 (Asn to Ala). An example of an Fc sequence is shown in FIG. 9.

In certain embodiments, the present invention makes available isolated and/or purified forms of the BMP-3 propeptides, which are isolated from, or otherwise substantially free of, other proteins.

In certain embodiments, BMP-3 propeptides (unmodified or modified) of the invention can be produced by a variety of art-recognized techniques. For example, such BMP-3 propeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the BMP-3 propeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified BMP-3 propeptides may be produced by digestion of naturally occurring or recombinantly produced BMP-3 by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such propeptides may be produced from naturally occurring or recombinantly produced BMP-3 such as standard techniques known in the art, such as by chemical cleavage (e.g., cyanogen bromide, hydroxylamine).

In certain embodiments, the present invention contemplates making mutations in the proteolytic cleavage site of the BMP-3 sequence to make the site less susceptible to proteolytic cleavage. The result is a BMP-3 polypeptide containing both propeptide and mature portion, which may be useful as a BMP-3 antagonist. More preferably, the mature portion is engineered with a stop codon, such that the BMP-3 propeptide is produced with some portion of the mature peptide attached. In one specific embodiment, a mutant may contain a point mutation at amino acids 357, 358, 359, 360, 361 or 362 of SEQ ID NO: 3, or at amino acids 335, 336, 337, 338, 339 or 340 of SEQ ID NO: 1. In another specific embodiment, such mutant may contain a point mutation at amino acids 364, 365, 366, 367 or 368 of SEQ ID NO: 4, or at amino acids 331, 332, 333, 334 or 335 of SEQ ID NO: 2.

3. Nucleic Acids Encoding BMP-3 Propeptides

In certain aspects, the invention provides isolated and/or recombinant nucleic acids encoding any of the BMP-3 propeptides, including functional variants, disclosed herein. For example, SEQ ID NOs: 5 and 6 encode BMP-3 propeptides. The subject nucleic acids may be single-stranded or double stranded. Such nucleic acids may be DNA or RNA molecules. These nucleic acids are may be used, for example, in methods for making BMP-3 propeptides or as direct therapeutic agents (e.g., in a gene therapy approach).

The subject nucleic acids encoding BMP-3 propeptides are further understood to include nucleic acids that are variants of SEQ ID NOs: 5 and 6. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 5 and 6.

In certain embodiments, the invention provides isolated or recombinant nucleic acid sequences that are at least 80%, 85%, 90%, 95%, 97%, 98%, 99% or 100% identical to SEQ ID NO: 5 or 6. One of ordinary skill in the art will appreciate that nucleic acid sequences complementary to SEQ ID NO: 5 or 6, and variants of SEQ ID NO: 5 or 6 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 5 or 6, complement sequence of SEQ ID NO: 5 or 6, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 5-6 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a BMP-3 propeptide and operably linked to at least one regulatory sequence. Regulatory sequences are art-recognized and are selected to direct expression of the BMP-3 propeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a BMP-3 propeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant BMP-3 propeptides include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of a subject BMP-3 propeptide in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject BMP-3 propeptide in cells propagated in culture, e.g., to produce proteins, including fusion proteins or variant proteins, for purification.

This invention also pertains to a host cell transfected with a recombinant gene including a coding sequence (e.g., SEQ ID NO: 5 or 6) for one or more of the subject BMP-3 propeptides. The host cell may be any prokaryotic or eukaryotic cell. For example, a BMP-3 propeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject BMP-3 propeptides. For example, a host cell transfected with an expression vector encoding a BMP-3 propeptide can be cultured under appropriate conditions to allow expression of the BMP-3 propeptide to occur. The BMP-3 propeptide may be secreted and isolated from a mixture of cells and medium containing the propeptide. Alternatively, the propeptide may be retained cytoplasmically or in a membrane fraction and the cells harvested, lysed and the protein isolated. A cell culture includes host cells, media and other byproducts. Suitable media for cell culture are well known in the art. The propeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the propeptide. In a preferred embodiment, the BMP-3 propeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant BMP-3 propeptide, can allow purification of the expressed fusion protein by affinity chromatography using a $Ni^{2+}$ metal resin. The purification leader sequence can then be subsequently removed by treatment with enterokinase to provide the purified BMP-3 propeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies

Another aspect of the invention pertains to antibodies. An antibody that is specifically reactive with a mature BMP-3 polypeptide and which binds competitively with the BMP-3 propeptide may be used as a BMP-3 antagonist. For example, by using immunogens derived from a BMP-3 mature peptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the BMP-3 peptide, an antigenic fragment which is capable of eliciting an antibody response, or a fusion protein. In a preferred embodiment, the inoculated mouse does not express endogenous BMP3, thus facilitating the isolation of antibodies that would otherwise be eliminated as anti-self antibodies. Techniques for conferring immunogenicity on a protein or peptide include conjugation to carriers or other techniques well known in the art. An immunogenic portion of a BMP-3 peptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of a BMP-3, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with BMP-3 and monoclonal antibodies isolated from a culture comprising such hybridoma cells.

The term "antibody" as used herein is intended to include fragments thereof which are also specifically reactive with a subject BMP-3 peptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for a BMP-3 peptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to a BMP-3 peptide may comprise administering to a mouse an amount of an immunogenic composition comprising the BMP-3 propeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the BMP-3 peptide. Once obtained, a hybridoma can be propagated in a cell culture, optionally in culture conditions where the hybridoma-derived cells produce the monoclonal antibody that binds specifically to the BMP-3 peptide. The monoclonal antibody may be purified from the cell culture.

The adjective "specifically reactive with" as used in reference to an antibody is intended to mean, as is generally understood in the art, that the antibody is sufficiently selective between the antigen of interest (e.g., a BMP-3 peptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain aspects, the disclosure provides antibodies that bind to a BMP-3 propeptide. Such antibodies may be generated much as described above, using a propeptide or fragment thereof as an antigen. Antibodies of this type can be used, e.g., to detect BMP-3 propeptides in biological samples and/or to monitor BMP-3 propeptide levels in an individual. The level of BMP-3 propeptides may be measured in a variety of sample types such as, for example, in cells, and/or in bodily fluid, such as in whole blood samples, blood serum, blood plasma and urine. An antibody that binds to a BMP-3 propeptide can be used to stimulate BMP-3 activity, encouraging decreased bone growth or bone resorption. This may be desirable in various disorders, such as any hyperostosis, osteopoikilosis, osteopetrosis, osteosclerosis (e.g., resulting from renal insufficiency), pyknodysostosis, osteomyelosclerosis, and hyperphosphatasia.

5. Screening Assays

In certain aspects, the present invention relates to the use of the subject BMP-3 propeptides to identify compounds (agents) which are agonist or antagonists of the BMP-3 propeptides. Compounds identified through this screening can be tested in bone and/or cartilage tissues to assess their ability to modulate bone/cartilage growth in vitro. Optionally, these compounds can further be tested in animal models to assess their ability to modulate bone/cartilage growth in vivo.

There are numerous approaches to screening for therapeutic agents for modulating bone growth by targeting the BMP-3 propeptides. In certain embodiments, high-throughput screening of compounds can be carried out to identify agents that perturb BMP-3A propeptide-mediated effects on bone or cartilage growth, such by assessing the effects of such compounds on BMP-3 propeptide-mediated effects on the osteogenic activity of BMP-2. In certain embodiments, the assay is carried out to screen and identify compounds that specifically inhibit or reduce binding of a BMP-3 propeptide to its binding partner (e.g., a BMP-3 mature peptide). Alternatively, the assay can be used to identify compounds that enhance binding of a BMP-3 propeptide to its binding protein (e.g., a BMP-3 mature peptide). In a further embodiment, the compounds can be identified by their ability to interact with a BMP-3 propeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of bone or cartilage growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a BMP-3 propeptide and its binding protein (e.g., a BMP-3 mature peptide).

Merely to illustrate, in an exemplary screening assay of the present invention, the compound of interest is contacted with an isolated and purified BMP-3 propeptide which is ordinarily capable of binding to a BMP-3 mature peptide, as appropriate for the purpose of the assay. To the mixture of the compound and BMP-3 propeptide is then added a composition containing a BMP-3 mature peptide. Detection and quantification of BMP-3 propeptide complexes provides a means for determining the compound's efficacy at inhibiting (or potentiating) complex formation between the BMP-3 propeptide and its binding protein (e.g., a BMP-3 mature peptide). The efficacy of the compound can be assessed by generating dose response curves from data obtained using various concentrations of the test compound. Moreover, a control assay can also be performed to provide a baseline for comparison. For example, in a control assay, isolated and purified BMP-3 mature peptide is added to a composition containing the BMP-3 propeptide, and the formation of BMP-3 propeptide/mature peptide complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the BMP-3 propeptide and its binding protein may be detected by a variety of techniques. For instance, modulation of the formation of complexes can be quantitated using, for example, detectably labeled proteins such as radiolabelled (e.g., $^{32}P$, $^{35}S$, $^{14}C$ or $^{3}H$), fluorescently labeled (e.g., FITC), or enzymatically labeled BMP-3 propeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a BMP-3 propeptide and its binding protein (e.g., a BMP-3 mature peptide). Further, other modes of detection such as those based on optical waveguides (PCT Publication WO 96/26432 and U.S. Pat. No. 5,677,196), surface plasmon resonance (SPR) (the mode employed by BiaCore systems used in the Examples, below), surface charge sensors, and surface force sensors are compatible with many embodiments of the invention.

Moreover, the present invention contemplates the use of an interaction trap assay, also known as the "two hybrid assay," for identifying agents that disrupt or potentiate interaction between a BMP-3 propeptide and its binding protein (e.g., a BMP-3 mature peptide). See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a BMP-3 propeptide and its binding protein (e.g., a BMP-3 mature peptide). See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; 5,965,368.

In one specific example, interaction between a BMP-3 propeptide and a mature BMP-3 peptide can be assayed by making a construct which expresses a FLAG-tagged BMP-3 precursor protein. The FLAG-tagged precursor protein is expressed in cells and processed into a BMP-3 propeptide and a FLAG-tagged mature BMP-3 peptide. The protein lysates prepared from the cells are then affinity-purified by antibodies against FLAG. Complexes containing a BMP-3 propeptide and a mature BMP-3 peptide can be determined by the presence of a BMP-3 propeptide in these affinity-purified protein samples (e.g., by immunoblot).

In certain embodiments, the subject compounds are identified by their ability to interact with a BMP-3 propeptide of the invention. The interaction between the compound and the BMP-3 propeptide may be covalent or non-covalent. For example, such interaction can be identified at the protein level using in vitro biochemical methods, including photocrosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a BMP-3 propeptide. This may include a solid phase or fluid phase binding event. Alternatively, the gene encoding a BMP-3 propeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for stimulating bone formation and increasing bone mass. Therefore, any compound identified using a cell-free system, or any other compound that is expected to affect BMP-3 function (e.g., antagonizing the osteogenic activity of BMP-2), can be tested in whole cells or tissues, in vitro or in vivo, to confirm their ability to modulate bone or cartilage growth. Various methods known in the art can be utilized for this purpose.

For example, BMP-3A inhibits BMP2-mediated induction of Msx2 and blocks BMP2-mediated differentiation of osteoprogenitor cells into osteoblasts. Thus, the effect of the BMP-3 propeptides or the test compounds on bone or cartilage growth can be determined by their effect on the osteogenic activity of BMP-2, for example, by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9).

Another example of cell-based assays includes analyzing the osteogenic activity of the subject BMP-3 propeptides and test compounds in mesenchymal progenitor and osteoblastic cells. To illustrate, recombinant adenoviruses expressing a human BMP-3 propeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

Further, the present invention contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

It is understood that the screening assays of the present invention apply to not only the subject BMP-3 propeptides and variants of the BMP-3 propeptides, but also any test compounds including agonists and antagonist of the BMP-3 propeptides. Further, these screening assays are useful for drug target verification and quality control purposes.

6. Methods of Administration

In certain embodiments, compositions (e.g., BMP-3 propeptides and compositions comprising such propeptides) of the present invention can be used for inducing bone and/or cartilage formation, preventing bone loss, increasing bone mineralization or preventing the demineralization of bone. For example, the subject BMP-3 propeptides and compounds identified in the present invention have application in treating osteoporosis and the healing of bone fractures and cartilage defects in humans and other animals. BMP-3 propeptides may be useful in patients that are diagnosed with subclinical low bone density, as a protective measure against the development of osteoporosis.

In a certain embodiment, the present invention provides methods of treating or preventing an individual suffering from a disease (disorder or condition) that is related to bone/cartilage defects through administering to the individual a therapeutically effective amount of a BMP-3 propeptide as described above. These methods are particularly aimed at therapeutic and prophylactic treatments of animals, and more particularly, humans.

In certain embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject BMP-3 propeptides may provide an environment to attract bone-forming cells, stimulate growth of bone-forming cells or induce differentiation of progenitors of bone-forming cells. BMP-3 propeptides of the invention may also be useful in the treatment of osteoporosis. Further, BMP-3 propeptides may be used in cartilage defect repair and prevention/reversal of osteoarthritis.

In certain embodiment, methods and compositions of the invention may also be used in wound healing and related tissue repair. The types of wounds include, but are not limited to, burns, incisions and ulcers. See e.g., PCT Publication No. WO84/01106.

In certain embodiment, the invention provides a therapeutic method and composition for repairing fractures and other conditions related to cartilage and/or bone defects or periodontal diseases. The invention further provides therapeutic methods and compositions for wound healing and tissue repair. Such compositions comprise a therapeutically effective amount of at least one of the BMP-3 propeptide of the invention in admixture with a pharmaceutically acceptable vehicle, carrier or matrix.

In certain specific embodiments, methods and compositions (e.g., BMP-3 propeptides) of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenyloin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss in part because of the effects of bacterial toxins and in part because of the effects of prolonged inflammation.

In certain embodiments, the present invention provides methods and therapeutic agents, for example, antagonists of BMP-3 propeptides, for treating diseases or disorders associated with abnormal or unwanted bone growth. For example, patients having the disease known as Fibrodysplasia Ossificans Progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which antagonists of BMP-3 propeptides may be therapeutically useful. Antagonists of BMP-3 propeptides may also be useful for treating other forms of abnormal bone growth, such as the pathological growth of bone following trauma, burns or spinal cord injury. In addition, antagonists of BMP-3 propeptides may be useful for treating or preventing the undesirable actions of BMPs associated with the abnormal bone growth seen in connection with metastatic prostate cancer or osteosarcoma. Examples of these antagonists of BMP-3 propeptides include, but are not limited to, compounds that disrupt interaction between a BMP-3 propeptide and its binding partner (e.g., a BMP-3 mature peptide) and antibodies that specifically bind to a BMP-3 propeptide.

In certain embodiments of the subject methods, one or more BMP-3 propeptides can be administered, together (simultaneously) or at different times (sequentially or overlapping). In addition, BMP-3 propeptides can be administered with another type of osteogenic, cartilage-inducing or bone-inducing factor. The two types of compounds may be administered simultaneously or at different times. It is expected that the BMP-3 propeptides of the invention may act in concert with or perhaps synergistically with other osteogenic, cartilage-inducing or bone-inducing factors. A variety of osteogenic, cartilage-inducing and bone-inducing factors have been described, particularly bisphosphonates. See e.g., European Patent Application Nos. 148,155 and 169,016. For example, other factors that can be combined with the subject BMP-3 propeptides include various growth factors such as epidermal growth factor (EGF), platelet derived growth factor (PDGF), transforming growth factors (TGF-α and TGF-β), and insulin-like growth factor (IGF).

7. Pharmaceutical Compositions

In certain embodiments, compounds (e.g., BMP-3 propeptides) of the present invention are formulated with a pharmaceutically acceptable carrier. For example, a BMP-3 propeptide (including, for example, an Fc fusion protein thereof) can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is generally in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-3 propeptides which may also optionally be included in the composition as described above, may alternatively or additionally, be administered simultaneously or sequentially with the BMP-3 propeptides in the methods of the invention. Preferably for bone and/or cartilage formation, the composition would include a matrix capable of delivering the BMP-3 propeptides or other therapeutic compounds to the site of bone and/or cartilage damage, providing a structure for the developing bone and cartilage and optimally capable of being resorbed into the body. For example, the matrix may provide slow release of the BMP-3 propeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., a BMP-3 propeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more BMP-3 propeptides in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician or veterinarian considering various factors which modify the action of the subject compounds of the invention (e.g., BMP-3 propeptides). The various factors include, but are not limited to, amount of bone weight desired to be formed, the site of bone damage, the condition of the damaged bone, the size of a wound, type of damaged tissue, the patient's age, sex, and diet, the severity of any infection, time of administration, and other clinical factors. Optionally, the dosage may vary with the type of matrix used in the reconstitution and the types of compounds in the composition. The addition of other known growth factors to the final composition, may also effect the dosage. Progress can be monitored by periodic assessment of bone growth and/or repair, for example, X-rays, histomorphometric determinations, and tetracycline labeling.

Exemplification

The invention now being generally described, it will be more readily understood by reference to the following examples, which are included merely for purposes of illustration of certain embodiments and embodiments of the present invention, and are not intended to limit the invention.

EXAMPLE 1

Construction, Expression, and Purification of BMP3 pro-MuIgG2a (BMP3 pro) Fusion A BMP3 propeptide (BMP3-pro) sequence was PCR amplified from a full length BMP3 cDNA and cloned into a human CMV derived expression vector in such a way that upon ligation it gave a fusion peptide with murine IgG2a. This construct (referred to as BMP3 pro-MuIgG2a) was transiently transfected in HEK293 cells using polyethylenimine (PEI). After seven days, cells were harvested and conditioned media was collected for purification.

Recombinant murine BMP3 pro-MuIgG2a fusion was expressed in HEK293 cells and purified by protein A affinity chromatography. 1 liter batch of conditioned media was filtrated, concentrated and loaded on a 4 ml rProtein A Sepharose Fast Flow column (Amersham Biosciences) previously equilibrated with TBS (pH 8.0). After protein loading, the column was washed with 20 column volumes (CV) of TBS, 10 CV of TBS-0.05% Tween 20, followed by additional wash with 10 CV of TBS to remove non-specifically bound proteins. Bound BMP3 pro-MuIgG2a protein was eluted with 100 mM Glycine (pH 3.0). Eluted fraction was immediately neutralized by addition of 1 M Tris and dialyzed against PBS (pH 8.0). Protein concentration was determined by BSA Protein Assay (Pierce). Protein purity was determined by 4-12% SDS-PAGE using pre-cast gels (Invitrogen) followed by Sure Blue staining (Invitrogen). The purified BMP3 pro-MuIgG2a migrates as a broad band on 4-12% SDS-PAGE gel, which indicates high degree of glycosylation. Purified protein was additionally analyzed by size exclusion chromatography on Superose TM column (Pharmacia Biotech). LAL assay was performed on the purified BMP3 pro-MuIgG2a and the amount of endotoxin detected was <0.5 U.

FIG. 10 shows BMP3 pro-MuIgG2a peptide Fc purified using Protein A affinity step. Lane 1 indicates molecular weight markers, while Lane 2 shows BMP3 pro-MuIgG2a peptide Fc purified from conditioned media expressing BMP3 pro-MuIgG2a peptide Fc using Protein A.

EXAMPLE 2

BMP3 pro-MuIgG2a Fusion Peptide Binds to Mature BMP-3

Immunoprecipitation studies were first carried out. Conditioned media was incubated with protein A beads, washed (3×) with Tris buffered saline containing 0.5% Tween 20 (TBST) to remove unbound protein. Mature BMP-3 was added and incubated overnight at 4° C. The beads were washed (3×) with TBST. The beads were resuspended in SDS sample buffer containing reducing agent and western blot analysis was performed with an anti-mature BMP-3 monoclonal antibody and detected with a HRP labeled anti-mouse IgG. As shown in FIG. 11, BMP3 pro-MuIgG2a peptide binds to mature BMP-3. Lane 1: Molecular Weight Markers. Lane 2: Control-incubation of protein A beads with conditioned media from 293 cells transfected with vector alone and mature BMP-3. Lane 3: Conditioned media from HEK293 cell expressing BMP3 pro-MuIgG2a-peptide incubated with BMP-3 and Protein A.

BiaCore chip analysis was also carried out. Purified BMP3 pro-MuIgG2a was coupled onto a BiaCore CM5 chip using the amine coupling procedure. As shown in FIG. 12, purified BMP3 pro-MuIgG2a binds to mature BMP-3 using BiaCore CM5 chip analysis. Mature BMP-3 was flowed over the chip and bound to BMP3 pro-MuIgG2a Fc (Panel A). In a control experiment, BSA was flowed over the chip but did not bind to BMP3 pro-MuIgG2a Fc (Panel B).

EXAMPLE 3

Mature BMP-3 Binds to Activin Receptor IIa (ActRIIa) and BMP3 pro-MuIgG2a Fc Competes with ActRIIa Binding to BMP-3

ActRIIa was immobilized on a BiaCore CM5 chip using standard amine coupling procedure. As shown in FIG. 13, mature BMP-3 (200 µg/ml) was injected on the ActRIIa coupled chip. BMP3 pro-MuIgG2a Fc (100 µg/ml) was injected onto the ActRIIa chip. Mature BMP-3 (200 µg/ml) and BMP3 pro-MuIgG2a (100 µg/ml)) were premixed and injected onto the ActRIIa coupled chip. As shown in FIG. 13, mature BMP-3 binds to ActRIIa (Trace A); BMP3 pro-MuIgG2a does not bind to ActRIIa (Trace B); and BMP3 pro-MuIgG2a Fc competes with ActRIIa binding to BMP-3 (Trace C).

Incorporation By Reference

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A pharmaceutical preparation for promoting bone growth and/or inhibiting bone loss, comprising:
   a) an isolated polypeptide comprising a BMP-3 propeptide that binds to a mature human BMP-3 polypeptide and;
   b) a pharmaceutically acceptable carrier, wherein the BMP-3 propeptide is selected from the group consisting of:
      i) a polypeptide comprising the amino acid sequence of SEQ ID NO: 1 and containing no more than 20 contiguous amino acids of the mature portion of a BMP-3 polypeptide;
      ii) a polypeptide comprising an amino acid sequence at least 95% identical to the amino acid sequence of SEQ ID NO: 1 and containing no more than 20 contiguous amino acids of a mature portion of a BMP-3 polypeptide; and
      wherein the pharmaceutical preparation does not contain mature BMP-3 protein, is pyrogen free, and is suitable for promoting bone growth and/or inhibiting bone loss in a human subject.

2. The pharmaceutical preparation of claim 1, wherein the BMP-3 propeptide comprises a polypeptide comprising an amino acid sequence at least 95% identical to the amino acid sequence of SEQ ID NO: 1, contains no more than 20 contiguous amino acids of a mature portion of a BMP-3 polypeptide, and comprises an alteration in the amino acid sequence of SEQ ID NO: 1 that alters glycosylation of the BMP-3 propeptide relative to SEQ ID NO: 1 when produced in a mammalian cell.

3. The pharmaceutical preparation of claim 1, wherein the BMP-3 propeptide comprises an alteration in the amino acid sequence of SEQ ID NO: 1 that decreases proteolytic cleavage of the BMP-3 propeptide relative to SEQ ID NO: 1.

4. The pharmaceutical preparation of claim 1, further comprising one or more other compounds selected from the group consisting of: a compound that inhibits bone resorption, a compound that stimulates bone formation, and a compound that increases bone mineral density.

5. The pharmaceutical preparation of claim 1, further comprising a bisphosphonate.

6. The pharmaceutical preparation of claim 1, wherein said BMP-3 propeptide is a fusion protein including, in addition to said BMP-3 propeptide domain, one or more polypeptide portions that enhance one or more of in vivo stability, in vivo half life, uptake/administration, tissue localization or distribution, formation of protein complexes, and/or purification.

7. The pharmaceutical preparation of claim 1, wherein said BMP-3 propeptide is a fusion protein including, in addition to said BMP-3 propeptide domain a polypeptide portion selected from the group consisting of: an immunoglobulin Fc domain and a serum albumin.

8. The pharmaceutical preparation of claim 6, wherein said fusion protein includes a purification subsequence selected from: an epitope tag, a FLAG tag, a polyhistidine sequence, and a GST fusion.

9. The pharmaceutical preparation of claim 1, wherein said BMP-3 propeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

10. The pharmaceutical preparation of claim 1, wherein the BMP-3 propeptide binds to a mature BMP-3 polypeptide with a $K_D$ of less than 1 micromolar.

11. The pharmaceutical preparation of claim 1, wherein the BMP-3 propeptide inhibits the interaction between a mature BMP-3 polypeptide and an ActRIIa polypeptide.

12. The pharmaceutical preparation of claim 1, wherein the BMP-3 propeptide inhibits the signaling mediated by interaction between a mature BMP-3 polypeptide and an ActRIIa polypeptide.

13. A BMP-3 propeptide fusion protein comprising: a BMP-3 propeptide and a second polypeptide portion, wherein the BMP-3 propeptide binds to a mature human BMP-3 polypeptide and is selected from the group consisting of:
- i) a polypeptide comprising the amino acid sequence of SEQ ID NO: 1 and containing no more than 20 contiguous amino acids of the mature portion of a BMP-3 polypeptide;
- ii) a polypeptide comprising an amino acid sequence at least 95% identical to the amino acid sequence of SEQ ID NO: 1 and containing no more than 20 contiguous amino acids of the mature portion of a BMP-3 polypeptide;

and, wherein the second portion is an IgG Fc domain.

14. A BMP-3 propeptide protein comprising: a BMP-3 propeptide and a second portion, wherein the BMP-3 propeptide binds to a mature human BMP-3 polypeptide and is selected from the group consisting of:
- i) a polypeptide comprising the amino acid sequence of SEQ ID NO: 1 and containing no more than 20 contiguous amino acids of the mature portion of a BMP-3 polypeptide;
- ii) a polypeptide comprising an amino acid sequence at least 95% identical to the amino acid sequence of SEQ ID NO: 1 and containing no more than 20 contiguous amino acids of the mature portion of a BMP-3 polypeptide;

and, wherein the second portion comprises a nonproteinaceous polymer.

* * * * *

UNITED STATES PATENT AND TRADEMARK OFFICE
CERTIFICATE OF CORRECTION

PATENT NO. : 7,625,867 B2
APPLICATION NO. : 11/092353
DATED : December 1, 2009
INVENTOR(S) : Knopf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 297 days.

Signed and Sealed this

Second Day of November, 2010

David J. Kappos
*Director of the United States Patent and Trademark Office*